United States Patent
Shibuya et al.

(10) Patent No.: US 10,011,812 B2
(45) Date of Patent: Jul. 3, 2018

(54) CULTURE CONTROL METHOD, CELL CULTURE APPARATUS, AND APPARATUS FOR EVALUATION OF CELLULAR CHARACTERISTICS

(71) Applicant: HITACHI, LTD., Tokyo (JP)

(72) Inventors: Keisuke Shibuya, Tokyo (JP); Ryoichi Haga, Tokyo (JP); Masaru Namba, Tokyo (JP); Kenichiro Oka, Tokyo (JP); Ken Amano, Tokyo (JP)

(73) Assignee: HITACHI, LTD., Tokyo (JP)

( * ) Notice: Subject to any disclaimer, the term of this patent is extended or adjusted under 35 U.S.C. 154(b) by 264 days.

(21) Appl. No.: 14/108,409

(22) Filed: Dec. 17, 2013

(65) Prior Publication Data

US 2014/0178996 A1  Jun. 26, 2014

(30) Foreign Application Priority Data

Dec. 26, 2012  (JP) .................................. 2012-283501

(51) Int. Cl.
| | |
|---|---|
| *C12M 1/34* | (2006.01) |
| *C12M 1/06* | (2006.01) |
| *C12M 1/42* | (2006.01) |
| *C12M 1/12* | (2006.01) |
| *C12M 1/36* | (2006.01) |

(52) U.S. Cl.
CPC ............ *C12M 41/42* (2013.01); *C12M 25/02* (2013.01); *C12M 27/02* (2013.01); *C12M 35/04* (2013.01); *C12M 41/32* (2013.01); *C12M 41/48* (2013.01)

(58) Field of Classification Search
CPC ..................................................... C12M 41/42
USPC .................................. 435/394, 289.1, 287.1
See application file for complete search history.

(56) References Cited

U.S. PATENT DOCUMENTS

| | | | | |
|---|---|---|---|---|
| 4,001,090 A | * | 1/1977 | Kalina ................ | B01F 3/04531 |
| | | | | 435/243 |
| 2006/0216818 A1 | * | 9/2006 | Amano ................ | C12M 41/48 |
| | | | | 435/287.5 |
| 2010/0081122 A1 | | 4/2010 | Shibuya et al. | |

FOREIGN PATENT DOCUMENTS

| | | | |
|---|---|---|---|
| JP | 61-149080 A | 7/1986 | |
| JP | H05-30962 A | 2/1993 | |
| JP | 2005261398 A | 9/2005 | |
| JP | 2006-296423 A | 11/2006 | |
| JP | 2008545410 A | 12/2008 | |
| JP | 2010081809 A | 4/2010 | |
| JP | 2010-178734 A | 8/2010 | |
| JP | 2011-36189 A | 2/2011 | |
| JP | 2012024045 A | 2/2012 | |
| WO | 98/22573 A1 | 5/1998 | |
| WO | WO-9822573 A1 * | 5/1998 | ............ C12M 21/08 |
| WO | 2006/127768 A2 | 11/2006 | |
| WO | 2007/117987 A2 | 10/2007 | |
| WO | 2012/085162 A1 | 6/2012 | |
| WO | WO 2012085162 A1 * | 6/2012 | ............ C12N 5/0694 |
| WO | 2012/174445 A1 | 12/2012 | |
| WO | 2012174460 A1 | 12/2012 | |

OTHER PUBLICATIONS

Nov. 17, 2015 Office Action issued in Japanese Application No. 2012-283501.
Feb. 23, 2016 partial European Search Report issued in European Application No. 13199072.3.
Jun. 24, 2016 extended European Search Report issued in Application No. 13199072.3.

* cited by examiner

*Primary Examiner* — Scott Long
*Assistant Examiner* — Nghi V Nguyen
(74) *Attorney, Agent, or Firm* — Oliff PLC

(57) ABSTRACT

This invention provides a culture control method and a cell culture apparatus that enable stable cell culture by regulating shear stress to be applied to cells within an adequate range. With the application of such culture control method and cell culture apparatus, cell culture is performed under agitation culture conditions in which the shear stress distribution is 0.5 Pa to 20 Pa in 80% or more of the culture vessel by volume.

8 Claims, 26 Drawing Sheets

(a) Top view (b) Side view (c) Cross-sectional view

CULTURE CONTROL METHOD, CELL CULTURE APPARATUS, AND APPARATUS FOR EVALUATION OF CELLULAR CHARACTERISTICS

TECHNICAL FIELD

The present invention relates to a culture control method that is employed when culturing cells that produce the main raw materials for pharmaceutical products and the like, a cell culture apparatus that employs such culture control method, and an apparatus for evaluation of cellular characteristics operated with the application of shear stress to cells.

BACKGROUND ART

Production of useful substances through cell culture of plant, microbial, animal, and other cells has been employed in different industries, including brewing and manufacturing of food, chemical, and pharmaceutical products. For example, pharmaceutical products, including antibody drugs, comprise as a main component a substance produced by animal cells, and such substance can be produced by culturing animal cells and separating and purifying the target substance secreted into the culture solution.

Cell culture techniques are classified into batch culture, continuous culture (perfusion culture), and fed-batch culture (semi-batch culture). Batch culture is carried out by preparing a fresh medium each time, inoculating cells thereinto, and performing culture without adding another medium before harvesting. While quality of the product varies with each culture, the risk of contamination can be dispersed and reduced. Continuous culture is carried out by feeding media to a culture system at a constant speed and simultaneously removing the same amount of the culture solution therefrom. Using continuous culture, the culture environment can be easily maintained in a constant state, and productivity is stable. However, contamination disadvantageously continues if the culture environment is contaminated even once. Fed-batch culture is carried out by adding a medium or a particular component of the medium during culture without removing the culture product until culture is terminated. Fed-batch culture is carried out by regulating the cell density so as to optimize the proliferative properties, and diluting useful substances accumulated in the culture system, so as to maintain productivity.

Production of useful substances necessitates the use of large-size animal cell culture vessels exhibiting a high production yield. Sufficient aeration and agitation are required for large-size culture vessels in order to supply oxygen to be absorbed by cells and to remove carbon dioxide discharged by cells. However, shear stress applied through excessive agitation and bubble aeration damage cells, and such damage disadvantageously causes cell death. Accordingly, culture vessels are designed so as to minimize shear stress.

For example, JP 2006-296423 A describes a culture apparatus comprising a culture vessel, an agitation blade, and a drive control unit, and it discloses that the number of revolutions of the agitation blade is regulated, so as to prevent the cells from dying because of shear stress. Also, JP S61-149080 A (1986) discloses shear stress as a culture property that becomes uneven when the size of the apparatus is increased, and it also discloses a method for regulating shear stress. JP 2010-178734 A and JP2011-36189 A also disclose a technique for adequately designing the number of revolutions and the configuration of revolving blades in the culture vessel, as with JP 2006-296423 A, so as to reduce the shear stress applied to cells during culture, thereby avoiding cell death.

SUMMARY OF THE INVENTION

Object to be Attained by the Invention

It remained completely unknown how shear stress would affect cells during culture in a shear stress distribution that is significantly lower than the shear stress level at which cell death takes place during culture. Under the above circumstances, it is an object of the present invention to provide a culture control method that enables stable cell culture by regulating the shear stress to be applied to cells so as to keep it within an adequate range, a cell culture apparatus that employs such culture control method, and an apparatus for evaluation of cellular characteristics operated with the application of shear stress to cells.

Means for Attaining the Object

The present inventors have conducted concentrated studies in order to attain the above object. As a result, they discovered that stable cell culture could be performed by maintaining the shear stress level at a given level even if such stress level is significantly lower than the high shear stress level at which cell death takes place during culture. This has led to the completion of the present invention.

According to the culture control method of the present invention, cell culture is performed under agitation culture conditions in which the shear stress distribution is 0.5 Pa to 20 Pa in 80% or more of the culture vessel by volume. The cell culture apparatus of the present invention comprises: a culture vessel that is equipped with an agitation blade and a drive unit that allows the agitation blade to revolve; and a control unit that controls the drive unit, so as to maintain the agitation culture conditions in which the shear stress distribution is 0.5 Pa to 20 Pa in 80% or more of the culture vessel by volume.

The shear stress distribution in the culture vessel can be calculated by, for example, fluid analysis. By performing such fluid analysis, the value and the percentage volume with respect to the shear stress distribution can be calculated using the concentration of the culture solution, the viscosity of the culture solution, the configuration of the culture vessel, the configuration of the agitation blade, the wall surface conditions of the culture vessel, and the number of revolutions of the agitation blade as variables.

In the case of a culture vessel with a volume of 1 liter, an aspect ratio of 1:1, and a flat-paddle-shaped agitation blade, for example, the number of revolutions for agitation may be adjusted to be within a range from 200 rpm to 500 rpm. Thus, shear stress can be adjusted so as to remain within the range from 0.5 Pa to 20 Pa in 80% or more of the culture vessel by volume.

In the case of a culture vessel with a volume of 3 liters, an aspect ratio of 2:3, and a pitched-paddle-shaped agitation blade, for example, the number of revolutions for agitation may be adjusted to be within the range from 150 rpm to 300 rpm. Thus, shear stress can be adjusted to be within the range from 0.5 Pa to 20 Pa in 80% or more of the culture vessel by volume.

In the case of a culture vessel with a volume of 3 liters, an aspect ratio of 2:1, and a flat-paddle-shaped agitation blade, for example, the number of revolutions for agitation may be adjusted to be within the range from 100 rpm to 200 rpm. Thus, the shear stress can be adjusted to be within the range from 0.5 Pa to 20 Pa in 80% or more of the culture vessel by volume.

In the case of a culture vessel with a volume of 100 liters, an aspect ratio of 1:1, and a flat-paddle-shaped agitation blade, for example, the number of revolutions for agitation may be adjusted to be within the range from 50 rpm to 100 rpm. Thus, the shear stress can be adjusted to be within the range from 0.5 Pa to 20 Pa in 80% or more of the culture vessel by volume.

In the case of a culture vessel with a volume of 10 m$^3$, an aspect ratio of 1:1, and a pitched-paddle-shaped agitation blade, for example, the number of revolutions for agitation may be adjusted to be within the range from 15 rpm to 50 rpm. Thus, the shear stress can be adjusted to be within the range from 0.5 Pa to 20 Pa in 80% or more of the culture vessel by volume.

The apparatus for evaluation of cellular characteristics according to the present invention comprises: a support onto which cells are fixed via anchor molecules; a chamber comprising an inlet port at one end thereof and an outlet port at another end thereof in which the support is mounted between the inlet port and the outlet port; a culture solution feeder that supplies a culture solution at a desired flow rate from the inlet port toward the outlet port; and an analyzer that analyzes components contained in the culture solution discharged from the outlet port.

It is particularly preferable that the analyzer measure at least one indicator selected from the group consisting of the oxygen consumption rate, the lactic acid secretion rate, the ammonia secretion rate, the glucose consumption rate, the glutamine consumption rate, and the intracellular metabolic flux.

It is preferable for the apparatus for evaluation of cellular characteristics of the present invention that the flow rate of the culture solution to be fed to the chamber and the spatial height of the support mounted on the chamber be employed as operational factors and that the shear stress to be applied to the cells fixed to the support via anchor molecules be employed as a control factor.

In addition, it is preferable for the apparatus for evaluation of cellular characteristics of the present invention that shear stress of 0 to 200 Pa be applied to cells fixed via anchor molecules.

Effects of the Invention

With the use of the culture control method and the cell culture apparatus according to the present invention, stable cell culture can be performed by adjusting the shear stress to be applied to cells at adequate levels. With the use of the apparatus for evaluation of cellular characteristics according to the present invention, in addition, cellular conditions and characteristics when a given shear stress is applied to the cells can be accurately evaluated.

EMBODIMENTS FOR CARRYING OUT THE INVENTION

The culture control method, the cell culture apparatus, and the apparatus for evaluation of cellular characteristics can be employed for culture of cells that produce the main raw materials of pharmaceutical products and other purposes. Examples of materials to be produced include proteins, such as antibodies and enzymes, and physiologically active substances, such as low-molecular-weight compounds and high-molecular weight compounds. Examples of cells to be subjected to culture include animal cells, plant cells, insect cells, bacterial cells, yeast cells, fungal cells, and algal cells, with animal cells that produce proteins, such as antibodies and enzymes, being particularly preferable.

Figure 1:
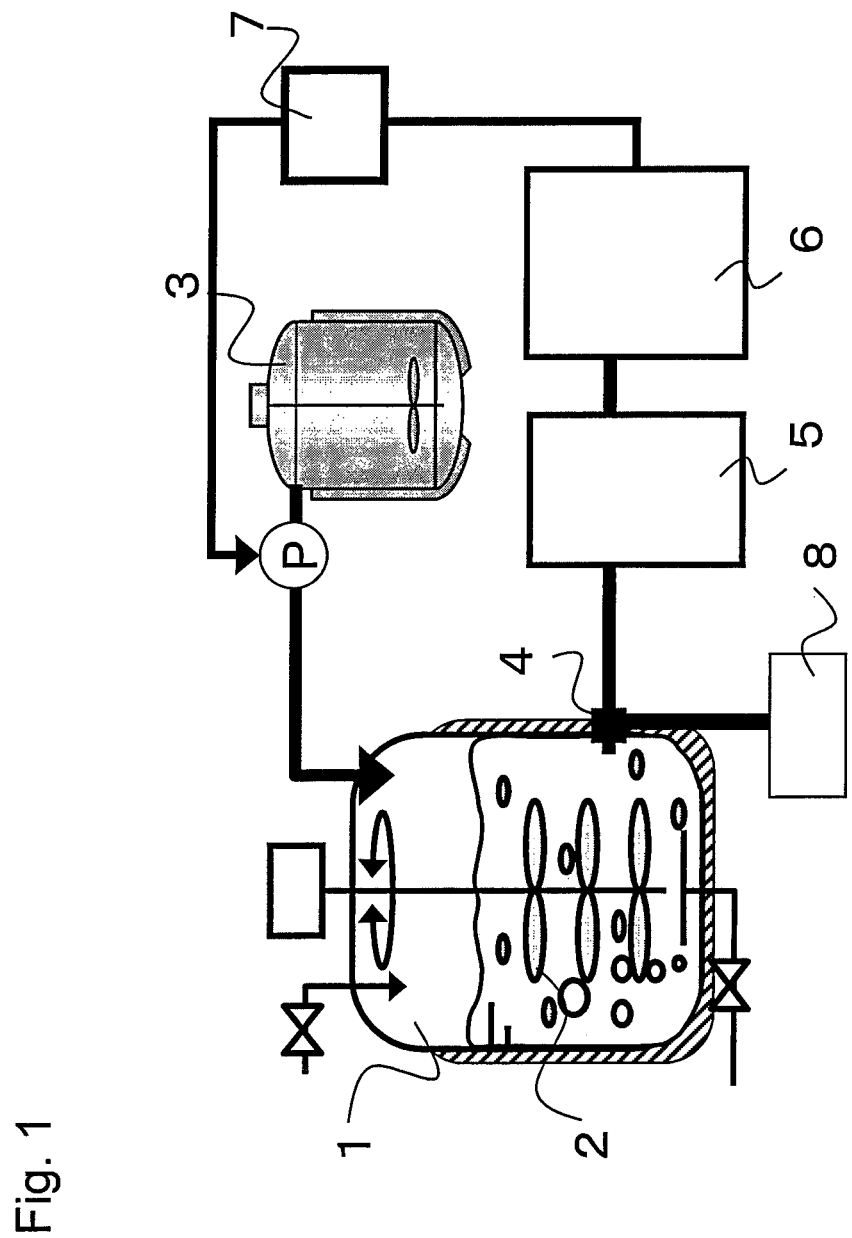
FIG. 1 shows the constitution of the culture apparatus.

As shown in FIG. 1, the cell culture apparatus is constituted by a culture vessel 1, an agitation blade 2, a medium-containing tank 3, an aseptic sampling unit 4, an assay device 5, an analyzer 6, and a control unit 7. While the cell culture apparatus shown in FIG. 1 is constituted so as to be suitable for fed-batch culture, the constitution is not limited thereto. When batch culture is performed, for example, the medium-containing tank can be omitted from the cell culture apparatus. When continuous culture is performed, the cell culture apparatus may comprise a groove through which a culture solution is discharged.

Concerning the culture control method and the cell culture apparatus, the shear stress distribution in 80% or more of the culture vessel 1 by volume is within the range from 0.5 Pa to 20 Pa. In other words, such apparatus employs a culture control method in which the shear stress distribution would be adjusted to be within the range from 0.5 Pa to 20 Pa in 80% or more of the culture vessel 1 by volume.

It is more preferable that the shear stress distribution be adjusted to be within the range from 0.5 Pa to 20 Pa in 90% or more of the culture vessel 1 by volume.

Stable cell culture can be performed by regulating the shear stress distribution so that it is within the range from 0.5 Pa to 20 Pa in 80% and preferably 90% of the culture vessel 1 by volume. When stable cell culture is performed, for example, the ratio of the amount of carbon source consumption (e.g., glucose) to the amount of growth inhibitor production (e.g., lactic acid) resulting from carbon source metabolism is constant. When such ratio is constant, it is not necessarily maintained, and it fluctuates without significant deviation. For example, such ratio fluctuates at about 10% above or below such constant level.

While the present inventors had studied the correlation between the shear stress and the cellular metabolism, they discovered the shear stress distribution effective for the production of useful substances (0.5 Pa to 20 Pa), which is lower than the high shear stress level at which cell death takes place. Hereafter, conditions for determination of an adequate shear stress distribution, the effects of culture resulting from patterns of shear stress levels, and the designing of a culture vessel realizing the adequate shear stress level are described in detail.

<Determination of Adequate Shear Stress Distribution>

In an agitation-type culture vessel, the shear stress distribution becomes uneven, and accurate evaluation of the correlation between shear stress and cellular metabolism becomes difficult. Accordingly, the present inventors prepared an apparatus for evaluation of the influence of shear stress utilizing characteristics of a micro flow channel and capable of application of uniform and strong shear stress to floating cells, and they evaluated the applicability of the apparatus to the designing of a culture vessel through culture experiments using Chinese hamster ovary (CHO) cells. While CHO cells are the target cells in the examples, cells of other types may also be targets.

1. Design of Apparatus for Evaluation of Influence of Shear Stress

Figure 2:
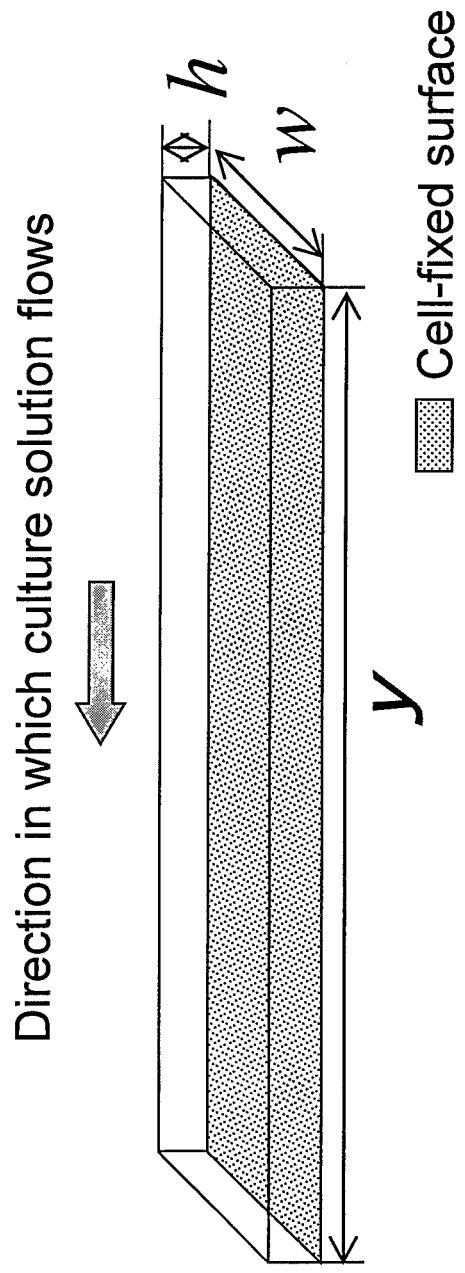
FIG. 2 shows the configuration of the fluid path in the apparatus for evaluation of the influence of shear stress.

A method for application of uniform and strong shear stress to adhesive cells was reported by Keane et al. (Biotechnol. Bioeng., Jan. 20, 2003; 81 (2): 211-20). In the case of the flow channel shown in FIG. 2, a laminar flow with a uniform shear stress (τw) is developed at the bottom of the flow channel in such a manner that the conditions represented by "h<<w" are satisfied. When the height of the flow channel is designated as "h" and changes in pressure loss of the culture solution in the flow direction are designated as "dp/dy," the size thereof can be represented by formula (1).

$$\tau_w = -\frac{h}{2} \times \frac{dp}{dy} \qquad (1)$$

Figure 3:
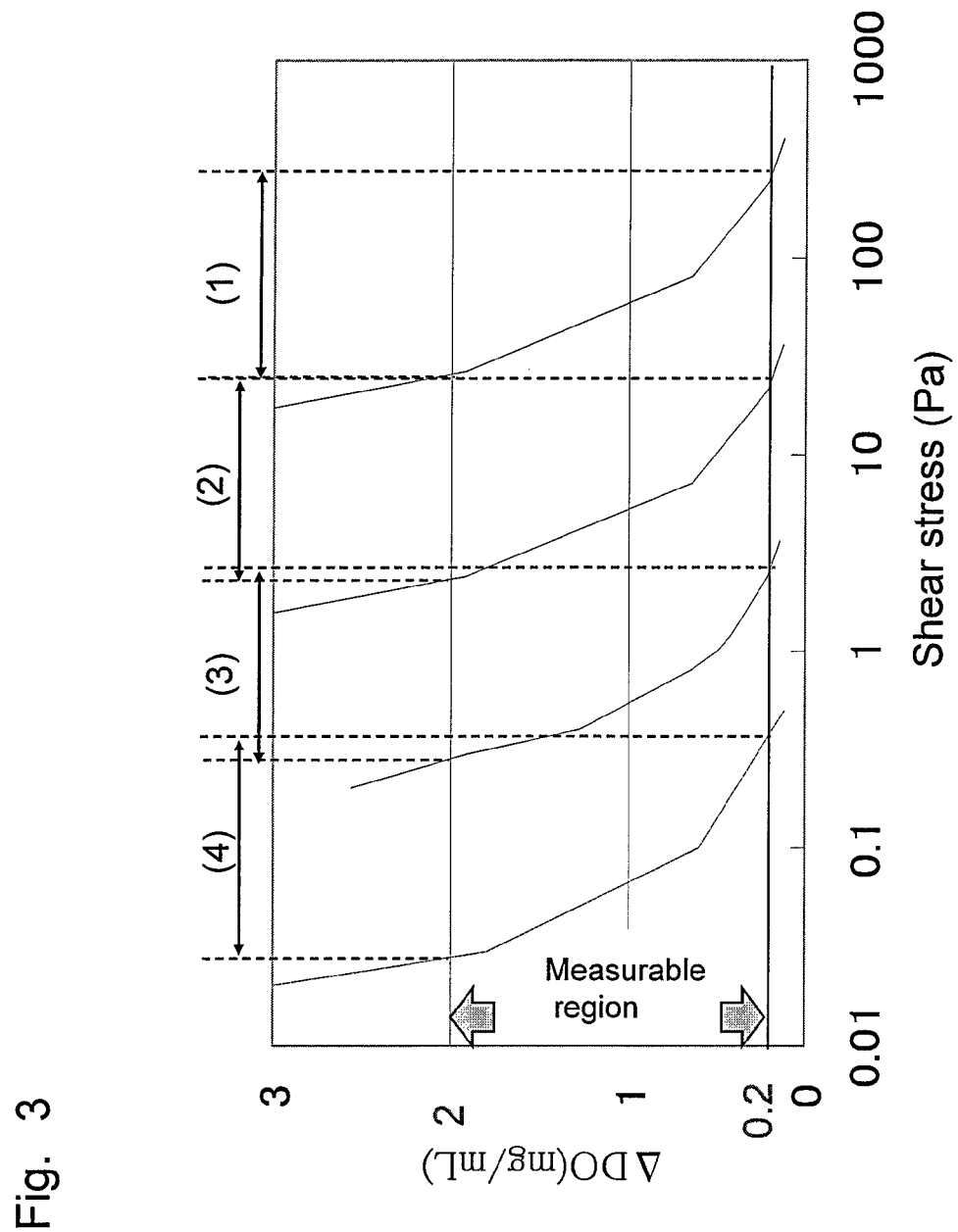
FIG. 3 shows the correlation between shear stress and oxygen consumption rate.

The flow chamber was designed as described below, so that it could measure the rate of oxygen consumption by cells and the speed of cellular metabolism. The oxygen consumption rate is determined based on the amount of dissolved oxygen decreased while it passes through a flow channel length with the length y. The amount of dissolved oxygen is measured at two points: the concentration of dissolved oxygen before it enters the flow chamber; and that immediately after it exits the flow chamber. When the culture solution flows too fast, the amount of dissolved oxygen decreased by cells is too small to measure. When the cellular respiration rate is $2\times10^{-12}$ mg/cell/sec and the density of the fixed cells is $1\times10^5$ cells/cm², specifically, the results of calculation using a standard system are as shown in FIG. 3. That is, the measurable range varies depending on flow channel height. An extensive range of shear stresses can be evaluated by preparing flow chambers with adequate flow channel heights. That is, the range shown in FIG. 3 (1) can be evaluated using a flow chamber with a flow channel height of 0.03 mm, the range shown in FIG. 3 (2) can be evaluated using a flow chamber with a flow channel height of 0.1 mm, the range shown in FIG. 3 (3) can be evaluated using a flow chamber with a flow channel height of 0.3 mm, and the range shown in FIG. 3 (4) can be evaluated using a flow chamber with a flow channel height of 0.8 mm. With the use of these four types of flow chambers, shear stress can be applied in the range of 0 Pa to 200 Pa.

In the case of floating cells, it is necessary to fix the cells onto the flow chamber. In order to fix cells without affecting cellular metabolism or other conditions, biocompatible anchors for membrane (BAM), which have proven records in the field of regenerative medicine and are less invasive for cells, are used as anchor molecules. A BAM chemical structure is shown below.

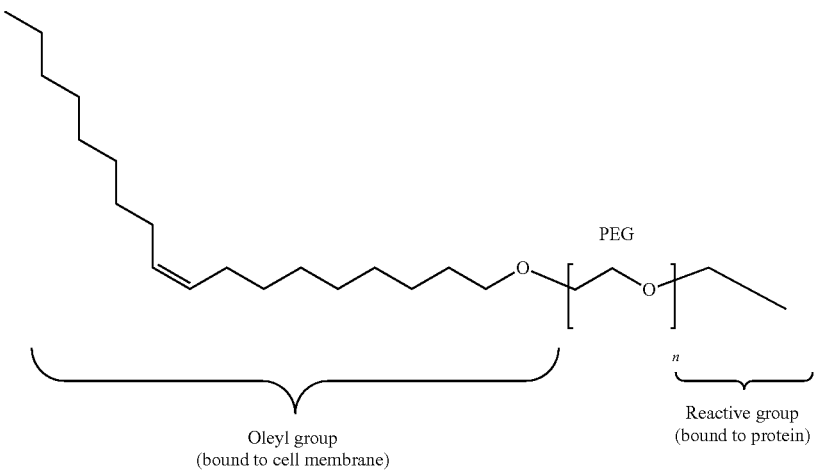

Oleyl group (bound to cell membrane)

Reactive group (bound to protein)

Figure 4:
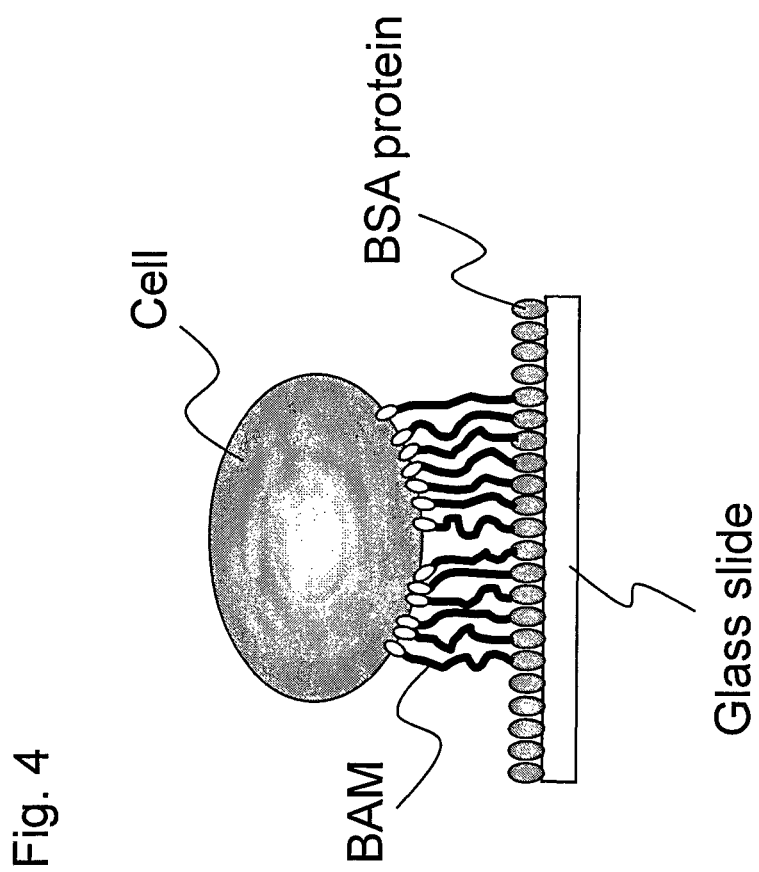
FIG. 4 schematically shows fixation via BAM.

BAMs represented by the above structural formula in which n is 20, 40, and 80 are referred to as BAM20, BAM40, and BAM80, respectively. FIG. 4 schematically shows cell fixation using BAM. As shown above, BAM has a reactive group binding to a protein and an oleyl group binding to a cellular membrane. For example, a BSA protein is allowed to bind to a support such as a glass plane. Thus, BAM serves as an anchor molecule and binds a cell to the support.

2. Constitution of an Apparatus for Evaluation of Cellular Characteristics

With the use of an apparatus for evaluation of cellular characteristics, uniform shear stress is applied to the cells fixed onto the support. Thus, changes in cellular metabolism or the like can be measured. Specifically, the apparatus for evaluation of cellular characteristics was designed to detect changes in the concentrations of media and components in the metabolites (i.e., glucose, glutamine, lactic acid, and ammonia) and in the concentration of dissolved oxygen.

Figure 5:
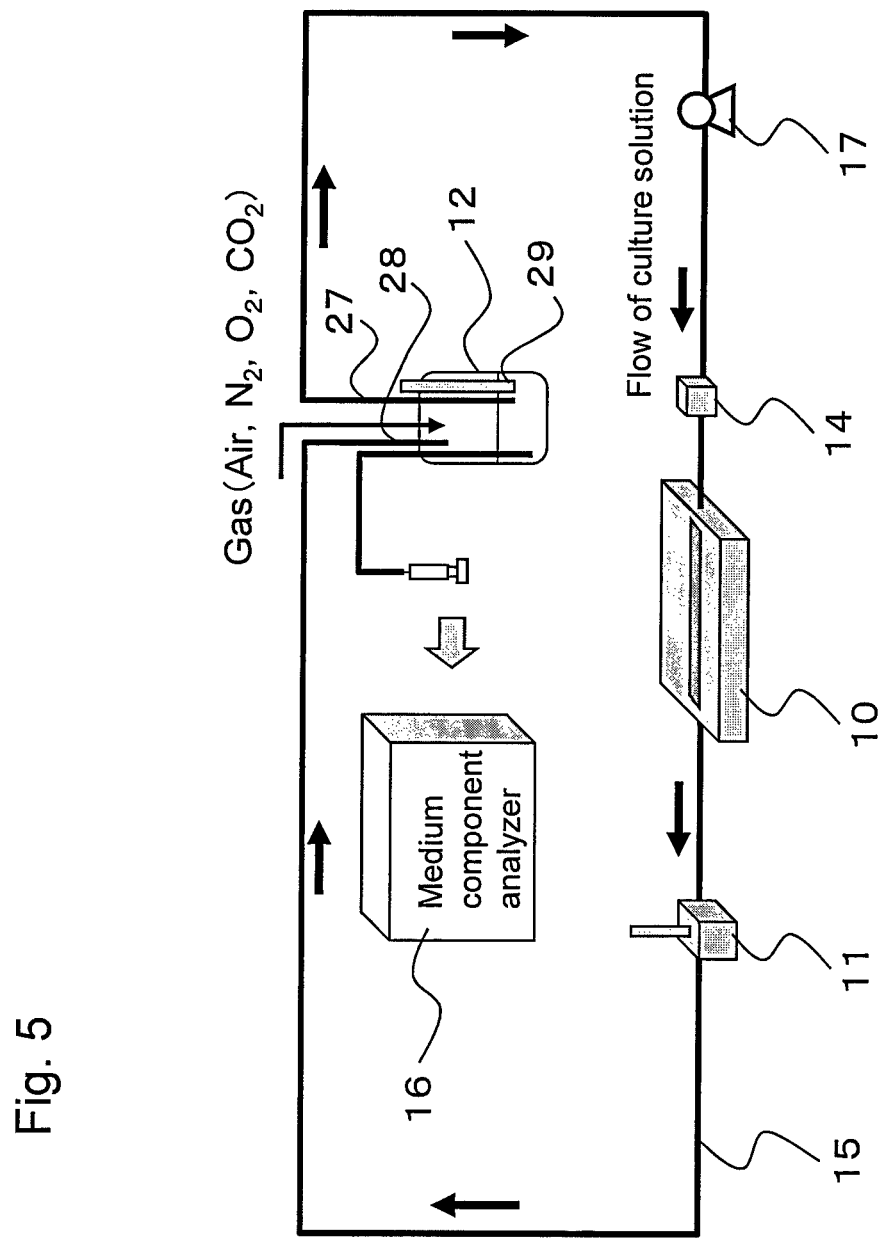
FIG. 5 shows the constitution of the apparatus for evaluation of the influence of shear stress.

As shown in FIG. 5, the apparatus for evaluation of cellular characteristics comprises a flow chamber 10, a dissolved oxygen (DO) measurement unit 11, a medium balancing tank 12, and a pulsation damper 14, and these components are connected to each other using a PharMed tube 15 with low gas permeability. Also, the apparatus for evaluation of cellular characteristics comprises an analyzer 16 that analyzes components of the culture solution sampled from the medium balancing tank 12. In addition, the apparatus for evaluation of cellular characteristics comprises a liquid delivery pump (Perista Pump) 17 provided in the middle of the PharMed tube 15.

In the apparatus for evaluation of cellular characteristics thus constituted, a culture solution is delivered with the aid of the liquid delivery pump 17 from the medium balancing tank 12 filled with a culture solution in which DO concentration, pH, and temperature are adjusted to given levels, the culture solution passes through the pulsation damper 14 that suppresses pulsation of the pump, and the culture solution is then delivered to the flow chamber 10 onto which the cells have been fixed. The culture solution discharged from the flow chamber 10 is delivered to the dissolved oxygen measurement unit 11, and the concentration of dissolved oxygen is then measured. The difference between the concentration of dissolved oxygen measured with the dissolved oxygen measurement unit 11 and the concentration of dissolved oxygen in the culture solution prepared in the medium balancing tank 12 may be calculated to determine the concentration of oxygen consumed by the cells.

Hereafter, components of the apparatus for evaluation of cellular characteristics are described in greater detail.

<Flow Chamber>

Figure 6:
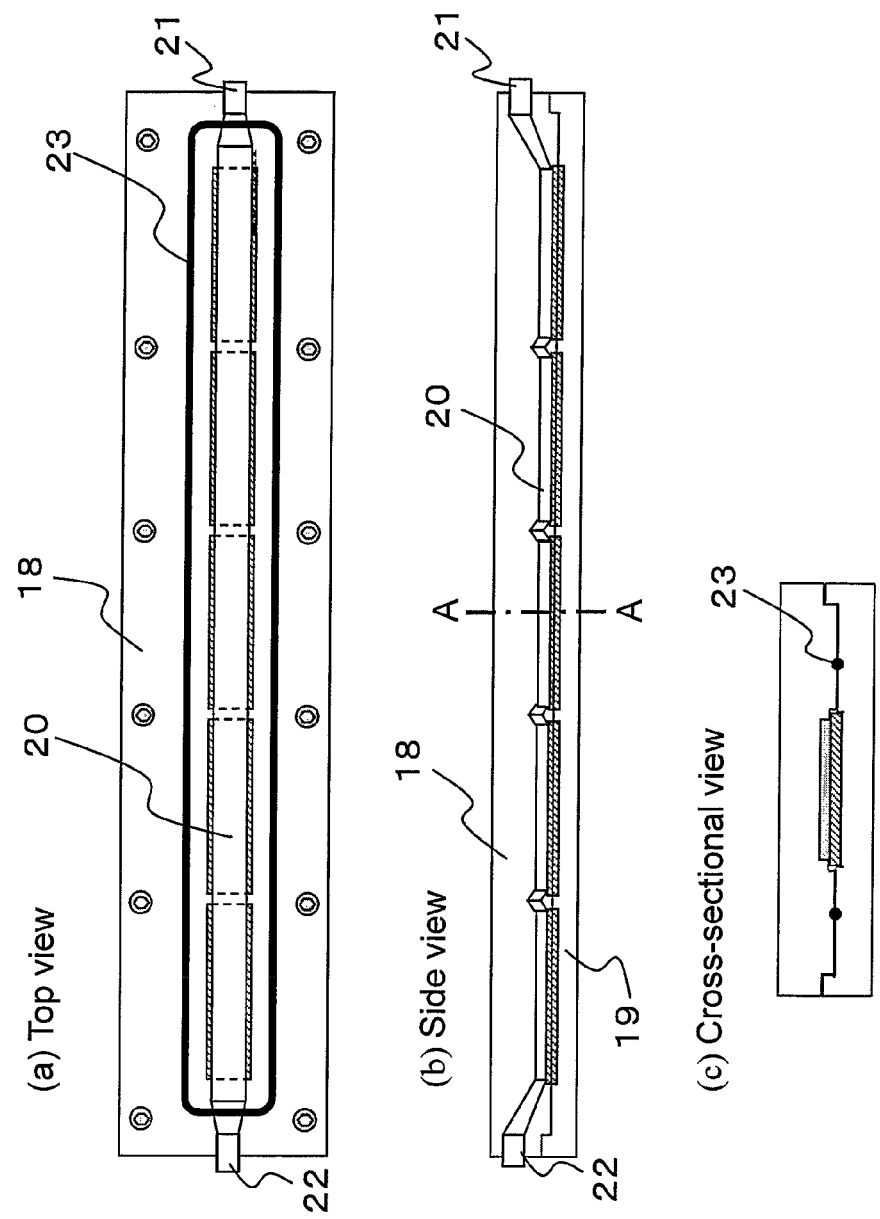
FIG. 6 schematically shows a flow chamber.

FIG. 6 schematically shows the flow chamber 10. FIG. 6 (a) is a top view of the flow chamber 10, FIG. 6 (b) is a side view of the flow chamber 10, and FIG. 6 (c) is a cross-sectional view taken along line A-A of FIG. 6 (b). The flow chamber 10 is composed of an upper member 18 and a lower member 19. In the flow chamber 10, there is a space 20 formed when the upper member 18 is connected to the lower member 19. In the space 20 of the flow chamber 10, an inlet port 21 is provided at one end in a longitudinal direction, and an outlet port 22 is provided at the other end.

The lower member 19 is provided with a recess that serves as the space 20 when it is connected to the upper member 18. A support comprising cells fixed thereon (e.g., a glass slide) can be mounted on the recess. Also, the upper member 18 is provided with a recess that serves as the space 20 when it is connected to the lower member 19. By adjusting a depth of the recess of the upper member 18, the height of the flow channel, h, shown in FIG. 2 can be brought to a desired level. Specifically, a plurality of the upper members 18 each having a recess with a different depth may be prepared, and an adequate upper member 18 to be used may be selected. Thus, the height of the flow channel, h, shown in FIG. 2 can be brought to a desired level. For example, four types of the upper members 18 (the upper members 18 with depths of 0.03 mm, 0.1 mm, 0.3 mm, and 0.8 mm) were provided in the present examples, as shown in FIG. 3 (1) to (4). In order to prevent the culture solution fed to the space 20 from leaking, a silicone O ring 23 was inserted between the upper member 18 and the lower member 19.

<Dissolved Oxygen (DO) Electrode>

Figure 7:
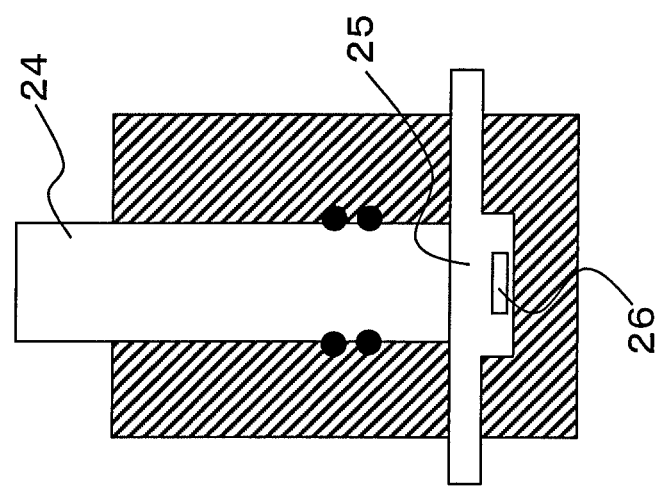
FIG. 7 shows a dissolved oxygen (DO) electrode flow cell.

FIG. 7 schematically shows the dissolved oxygen measurement unit 11. The apparatus for evaluation of cellular characteristics was constituted to allow the mounting of a commercially available dissolved oxygen (DO) electrode 24 thereon, and a sensor of the DO electrode 24 was located to face the space 25 through which the culture solution passes. While the DO electrode 24 measures oxygen that passes through a diaphragm (a gas-permeable membrane), oxygen is consumed in the region that is in contact with the diaphragm. Thus, the measured value would be smaller than the actual value, unless the flow rate is sufficiently high. In order to prevent such problem, the apparatus for evaluation of cellular characteristics comprises a space allowing revolution of an agitator 26 directly below the sensor of the DO electrode 24, in order to sufficiently perform agitation.

<Medium Balancing Tank>

A culture vessel and its control unit were used for the medium balancing tank 12. The culture vessel was provided with a medium outflow tube 27 and a medium inflow tube 28 in order to circulate the culture solution. The concentration of dissolved oxygen was maintained at a constant level (e.g., 2.7 mg/l) in the medium balancing tank through aeration of the air, nitrogen, and oxygen. The pH level was maintained at a constant level (e.g., 7.2) through aeration of carbon dioxide. The medium balancing tank comprises a DO electrode 29 for measuring the concentration of dissolved oxygen in the culture solution. In the medium balancing tank 12, the temperature of the culture solution can be maintained at, for example, 37° C. by heating the vessel with the aid of a heater (not shown).

<Liquid Delivery Pump and Pulsation Damper>

A Perista Pump was used as the liquid delivery pump 17. In order to eliminate pulsation of the liquid delivery pump 17, an O-Plus damper (Sigma-Aldrich) was used as the pulsation damper 14 to reduce the pressure fluctuation by 97%.

3. Method of Cell Culture Experiment Using the Apparatus for Evaluation of Cellular Characteristics of the Present Invention 3-1. Cells and Medium The experiment was performed using Chinese hamster ovary (CHO) cells (CRL-9606 cells for adhesion culture and float culture) producing glycoproteins, and tissue plasminogen activators (tPAs), purchased from the American Type Culture Collection (ATCC). In the present examples, adhesive cells were conditioned so as to become floating cells. The medium used was prepared by adding fetal bovine serum (FBS) (final concentration: 10%), glutamine at 0.58 g/l, glucose at 3.6 g/l, penicillin, and streptomycin to the Ham's F12 basal medium. For analysis of the intracellular metabolic flux, another medium was prepared in the same manner as described above, except that isotope-labeled glucose was used instead of glucose.

3-2. Method of Evaluation Test
<Cell Fixation to Glass Slide>

A solution of bovine serum albumin (BSA) dissolved at 10 mg/ml in phosphate buffered saline (PBS) (3 ml) was applied to a glass slide provided with a chamber, so that cell culture could be performed, and the glass slide was allowed to stand at 37° C. for 1 hour. After the resultant was washed three times with PBS, 3 ml of a solution of 100 μM anchor molecules (BAM20, BAM40, or BAM80) dissolved in PBS was added thereto, and the resultant was allowed to stand at 37° C. for 2 hours. After the resultant was washed three times with PBS, 2 ml of a cell suspension (0.75 cells/ml) was added thereto, culture was conducted for 1 day, and the culture product was used for shear stress evaluation. The above-described procedures were carried out aseptically in a clean bench using a sterilized solution, a glass slide, and the like.

<Sterilization of Apparatus for Evaluation of Cellular Characteristics>

Acecide 6% disinfectant (a hydrogen peroxide-based solution) was allowed to circulate in the apparatus for evaluation of cellular characteristics shown in FIG. 5 for 30 minutes in order to sterilize the inside of the flow channel, including the PharMed tube 15. Thereafter, a sterilized PBS solution was allowed to pass therethrough, so as to rinse the disinfectant away.

<Evaluation Test>

After sterilization, a glass slide with cells fixed thereto was mounted on the flow chamber 10, 200 ml of a medium was added to the medium balancing tank 12, and the liquid delivery pump 17 was activated to circulate the culture solution at a flow rate at which the shear stress of interest could be applied. The culture solution was sampled from the medium balancing tank 12 once every hour, and the concentrations of glucose, glutamine, lactic acid, and ammonia were measured using a medium component analyzer (Nova). The amount of glucose consumption, the amount of glutamine consumption, the amount of lactic acid secretion, and the amount of ammonia secretion were determined based on the absolute values of the differences in concentrations between the values at the initiation of culture and those 5 hours after the initiation of culture. The amount of oxygen consumption was determined by calculating the difference between the concentration of dissolved oxygen in the medium balancing tank 12 and the concentration of dissolved oxygen measured with the dissolved oxygen measurement unit 11 at the outlet port 22 of the flow chamber 10.

Figure 8:
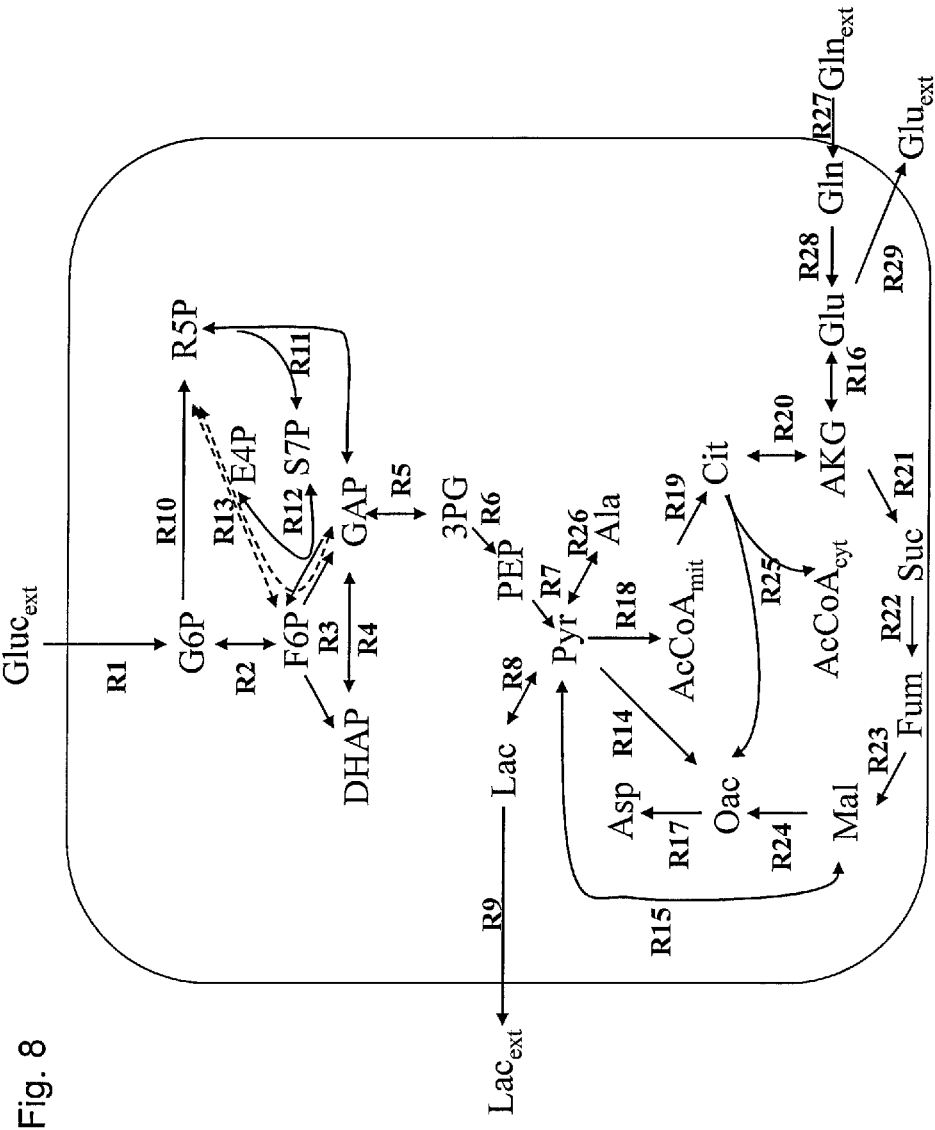
FIG. 8 shows an intracellular metabolic pathway.

3-3. Analysis of Intracellular Metabolic Flux (1) Prediction of Intracellular Metabolic Flux In simulations, it is necessary to predict the intracellular metabolic pathway of the cells to be analyzed. To this end, a metabolic pathway model commonly employed for animal cells shown in FIG. 8 was used. When simulating the intracellular metabolic flux, random metabolic flux values (R1 to R29 shown in FIG. 8) are first applied, and the percentage of carbon isotopes contained in cellular metabolites in the steady state is calculated with reference to the metabolic pathway shown in FIG. 8. The calculated value is compared with the percentage of carbon isotopes in cellular metabolites. When differences therebetween are statistically significant (i.e., when the values are different from each other), the mean square error of the percentage of carbon isotopes in the metabolites predicted via simulations and the percentage of carbon isotopes in metabolites measured via experiments is to be minimized by modifying the metabolic flux value determined via simulations. Thus, the percentage of carbon isotopes is determined. Until the statistical differences are eliminated, comparison of the percentage of carbon isotopes predicted via simulations and that actually measured as described above is repeated. While such ratio can generally be predicted by repeating calculations 2 or 3 times, statistically significant differences occasionally remain, regardless of the number of repetitions. In such a case, it should be determined that the employed metabolic pathway model is malfunctioning or the measured data are not accurate. According to the method of the present invention, in addition, the confidential intervals of the predicted values can be determined by a statistical procedure. First of all, the predicted metabolic flux values should be determined, one metabolic flux (e.g., R3) is selected from among the predicted metabolic flux values (R1 to R29), and the metabolic flux value is gradually increased. When a statistically significant difference appears as a result of comparison with the measured value, such value is designated to be the upper limit of the metabolic flux. The lower limit is determined by gradually decreasing the deduced flux value and detecting the statistically significant difference. Other metabolic fluxes are successively subjected to this procedure, and the confidence intervals can be determined for all the metabolic fluxes.

While the simulations described above require observation parameters obtained via experiments (i.e., the percentage of carbon isotopes in intracellular metabolites and the extracellular metabolic flux), in general, necessary observation parameters vary depending on the target cells or media to be used. According to the method of the present invention, four types of extracellular fluxes (i.e., glutamine, glucose, lactic acid, and glutamic acid) and 13 types of intracellular metabolites (i.e., Pyr, Lac, Ala, Gly, Suc, Fum, Ser, Akg, Mal, Asp, Glu, Gln, and Cit) were employed as observation parameters. The intracellular metabolic flux analysis requires input parameters (i.e., the intracellular metabolite and the extracellular metabolic flux values).

(2) Measurement of Intracellular Metabolite

Measurement of intracellular metabolites comprises three steps: (i) extraction of intracellular metabolites; (ii) preparation of metabolite derivatives; and (iii) GC/MS analysis. Such measurement is described below in detail.

(i) Extraction of Intracellular Metabolite

Figure 9:
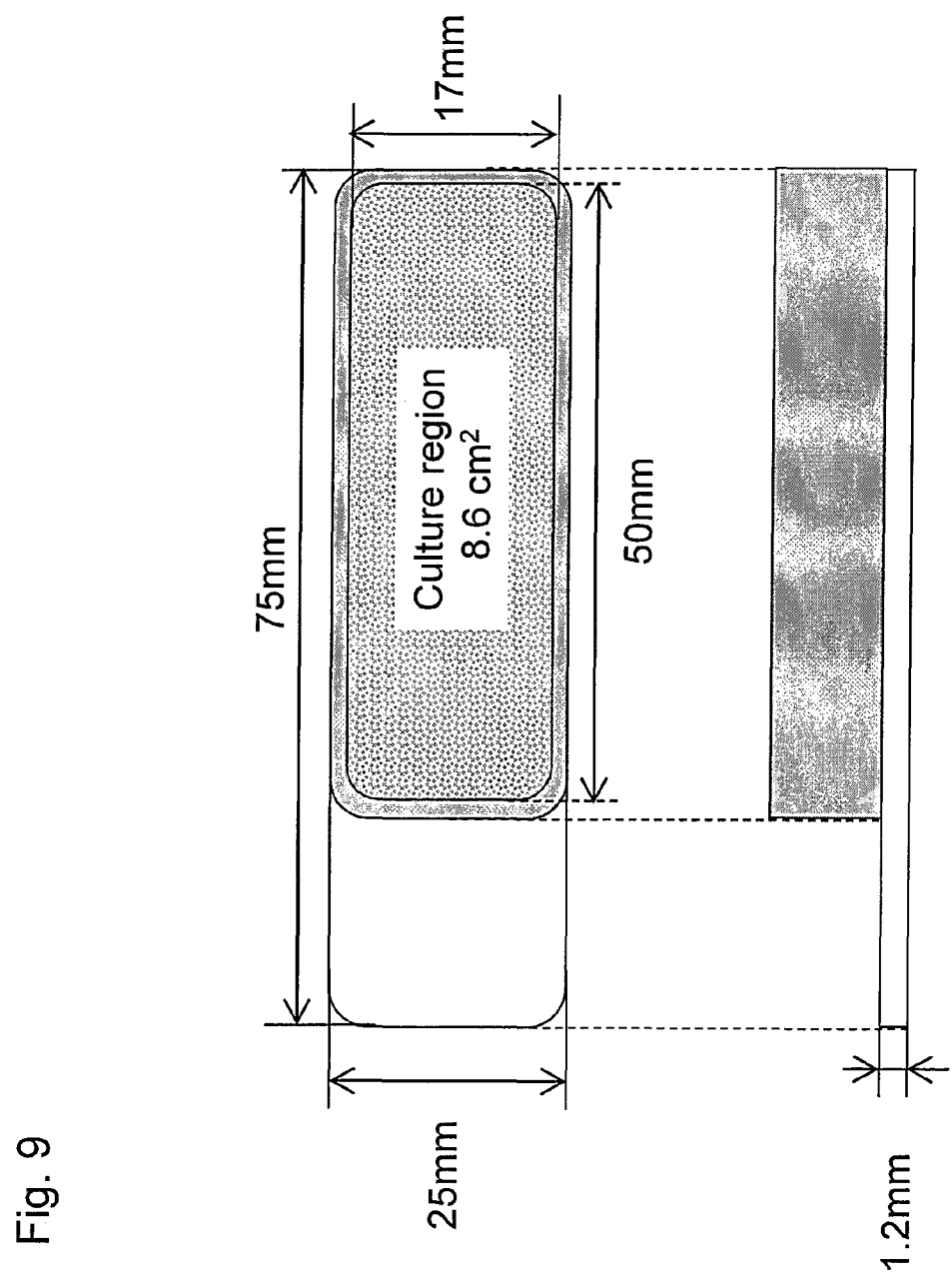
FIG. 9 shows a glass slide and a chamber.

A chamber of the size shown in FIG. 9 was mounted on the glass slide, CHO cells (CRL-9606 cells) fixed to the glass slide were washed once in PBS, 200 μl of methanol cooled to −20° C. was added, and distilled water at 4° C. was successively added in amounts of 600 μl each. After ultrasonication was conducted for 1 minute, 5 μl of 2 mg/ml norvaline was added thereto, and 800 μl of chloroform was further added. The resultants were mixed with the aid of a vortex mixer at 4° C. for 30 minutes, the mixture was centrifuged using a centrifuge (Microfuge®, Beckman Coulter) at 11,500 rpm and 4° C. for 30 minutes, and the upper layer of the two separate layers was transferred to another microtube. The resultant was dried by evaporation overnight.

(ii) Preparation of Metabolite Derivatives

To the dried sample, 2% methoxyamine hydrochloride (Pierce) was successively added in amounts of 30 μl each, the resultant was lightly mixed using a vortex mixer, the solution was collected in the lower side of the center of the culture vessel using a tabletop centrifuge, and the reaction was allowed to proceed on a heating block at 55° C. for 2 hours. A solution of MBTSTFA+1% TBDMCS (Pierce) was successively added in amounts of 45 each, the resultant was lightly mixed using a vortex mixer, the solution was collected in the lower side of the center of the culture vessel using a tabletop centrifuge, and the reaction was allowed to proceed on a heating block at 37° C. for 1 hour. The reaction solution was transferred to a vessel for GC/MS analysis and stored at room temperature until analysis was initiated.

(iii) GC/MS Analysis

GC/MS analysis was carried out using the Agilent GC-MS System and the 30 m DB-35MS capillary column with a temperature gradient of 100° C. to 300° C. at a rate of 3.5° C./min. Analysis was carried out at an inlet port temperature of 270° C. with the use of helium as carrier gas at a flow rate of 1 ml/min.

4. Results of Culture Experiment Using the Apparatus for Evaluation of Cellular Characteristics of the Present Invention 4-1. Fixation of Floating Cells There are three types of anchor molecules (BAMs) used for cell fixation: BAM20, BAM40, and BAM80, depending on molecular weight. It is necessary to select adequate anchor molecules in accordance with cell type. Thus, adequate anchor molecules (BAMs) were selected in accordance with the following evaluation indicators: (1) adhesiveness; and (2) cellular metabolism.

(1) Evaluation of Adhesiveness

Anchor molecules (BAM20, BAM40, and BAM80) were applied to a glass slide, cells were seeded thereon, culture was conducted for 1 day, and the number of floating cells thereafter was measured. As a result, the number of floating cells was found to be greater in descending order from cells coated with BAM40, those with BAM20, those with BAM80, and those without coating.

(2) Evaluation of Cellular Metabolism

Figure 10:
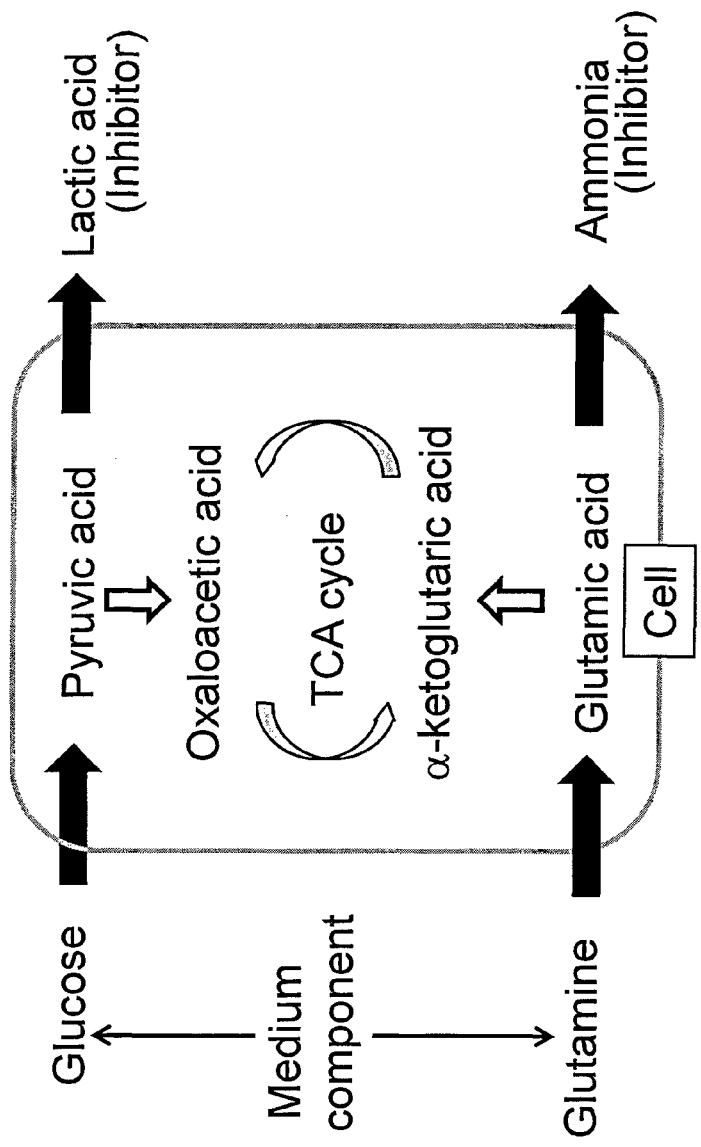
FIG. 10 schematically shows the intracellular metabolism.

The trends in changes of cellular metabolism can be perceived by analyzing culture solutions. FIG. 10 schematically shows intracellular metabolism. While glucose as a nutrient substrate is metabolized mainly by lactic acid, a part thereof is used for energy production in the TCA cycle. Similarly, glutamine is metabolized mainly by ammonia, and a part thereof is used for energy production. By measuring changes in the concentration of glucose, glutamine, lactic acid, and ammonia in culture solutions, the lactic acid secretion/glucose consumption rate (the glucose-lactic acid metabolic system) and the ammonia secretion/glutamine consumption rate (the glutamine-ammonia metabolic system) can be determined and evaluated as changes of metabolism.

Figure 11:
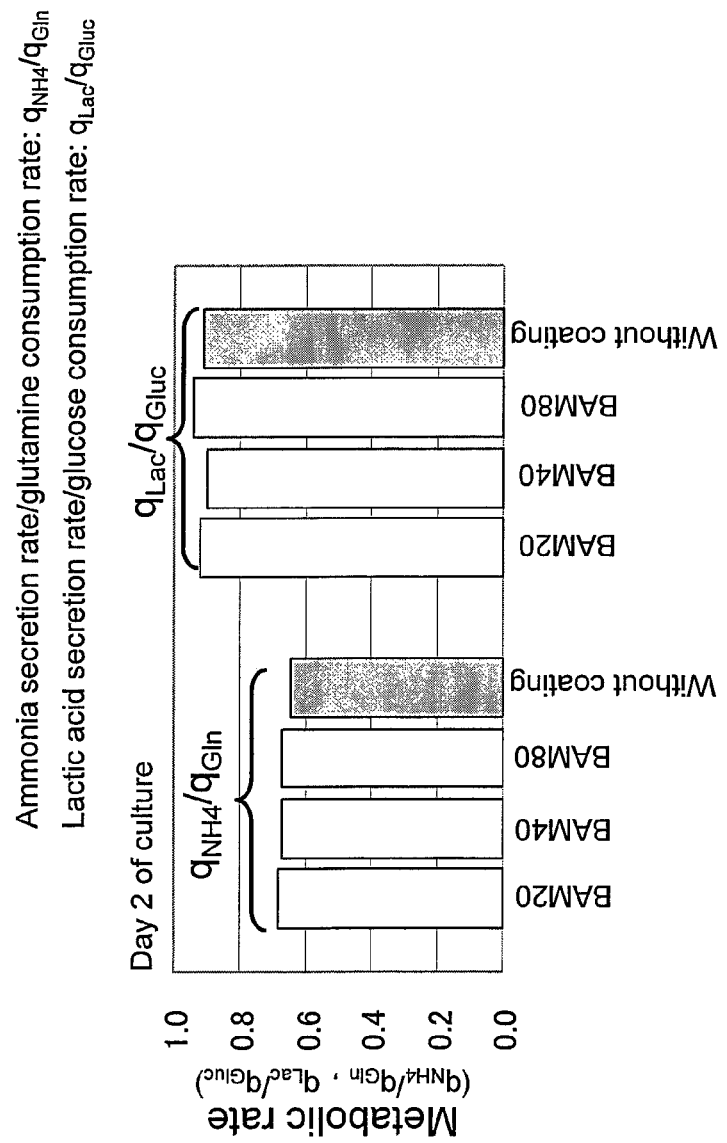
FIG. 11 shows the results of measurement of changes in cellular metabolism caused by BAM fixation.

Cells are fixed with the aid of anchor molecules (BAM20, BAM40, and BAM80), and changes in cellular metabolism are measured. FIG. 11 shows the results of measurement. In comparison with the cells without anchor molecules (i.e., cells without coating), none of the anchor molecules showed significant differences, and no influence was observed on cellular metabolism. This indicates that fixation would not affect cellular metabolism.

As a result of evaluation of (1) adhesiveness and (2) cellular metabolism, use of BAM40 anchor molecules was determined to be suitable for floating CHO cells (CRL-9606 cells) because of the high adhesiveness thereof and the lack of influence thereof on the cellular metabolism.

Figure 12:
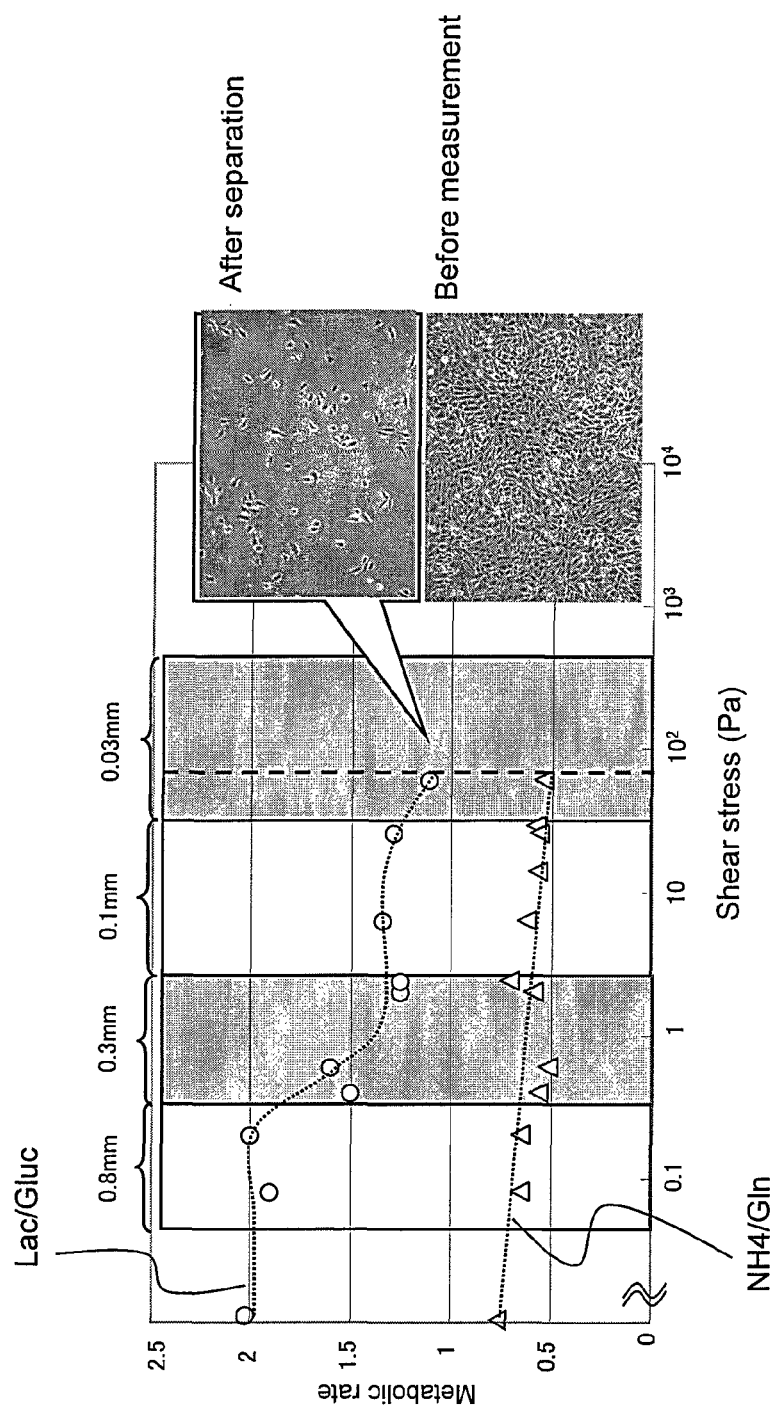
FIG. 12 shows changes in the metabolism caused under different shear stress levels.
Figure 13:
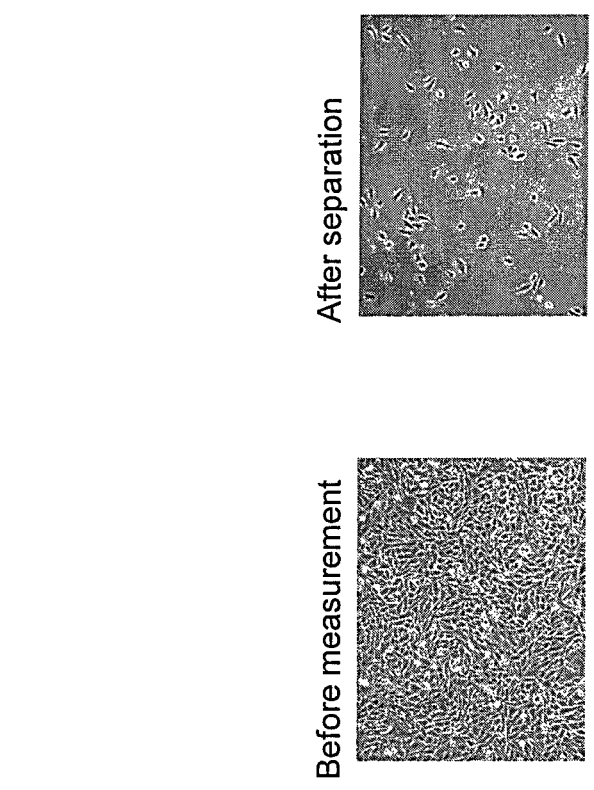
FIG. 13 shows a photograph showing the cellular conditions before shear stress application and a photograph showing the cellular conditions after shear stress application.

4-2. Evaluation of Culture Using an Apparatus for Evaluation of Cellular Characteristics While the floating CHO cells (CRL-9606 cells) were fixed on the glass slide, shear stress of 0.1 Pa to 200 Pa was continuously applied, and changes of metabolism under various shear stress conditions were assayed (the value at the shear stress of 0 Pa indicates the data attained via stationary culture). FIG. 12 shows the assay results. As shown in FIG. 12, the metabolism did not change in terms of the lactic acid secretion/glucose consumption rate with the application of shear stress of 0.6 Pa or lower, and a significant decrease was observed in the metabolic rate at shear stress of 0.6 Pa to 2 Pa, in comparison with stationary culture. The metabolism remained at a constant level with the application of shear stress of 2 Pa to 30 Pa. Since the cells were peeled from the glass slide with the application of shear stress greater than 100 Pa, the shear stress distribution that can be evaluated with the apparatus for evaluation of cellular characteristics of the present invention was determined to be 100 Pa or lower. FIG. 13 shows a photograph showing the cell conditions before shear stress application and a photograph showing the cell conditions after application of shear stress greater than 100 Pa.

In terms of the ammonia secretion/glutamine consumption rate, as shown in FIG. 12, the metabolic rate was gradually decreased as shear stress was elevated. While changes in intracellular metabolism could not be detected via a conventional laboratory-scale experiment (with shear stress up to 1 Pa), changes in intracellular metabolism caused by shear stress were evaluated for the first time with the use of the apparatus for evaluation of cellular characteristics of the present invention.

4-3. Application of Metabolic Flux Analysis

Figure 14:
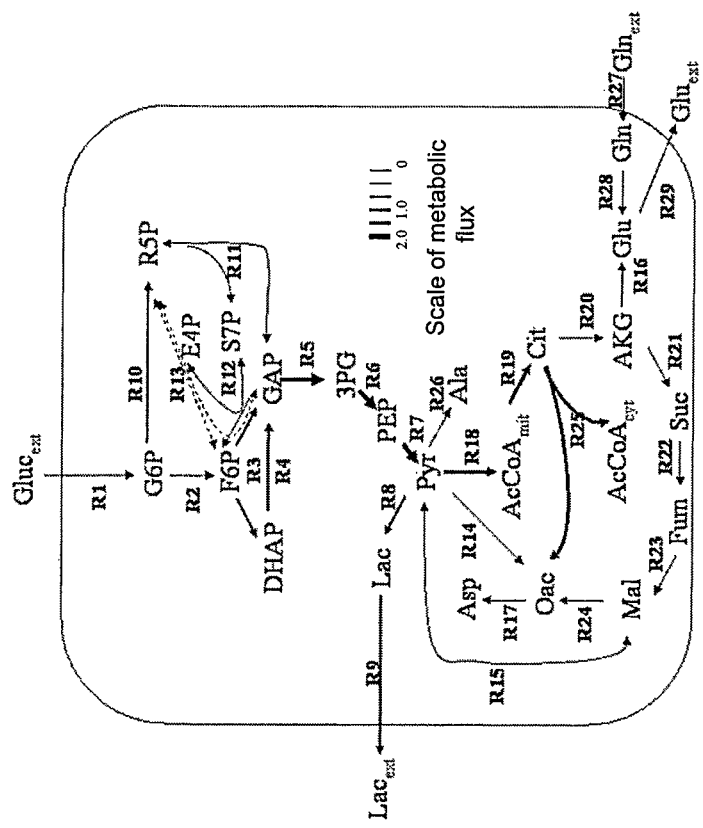
FIG. 14 shows the results of analysis of intracellular metabolic flux using an apparatus for evaluation of the influence of shear stress.

The cells to which shear stress of 0.1 Pa had been applied were subjected to intracellular metabolism analysis using an apparatus for evaluation of cellular characteristics. The results are shown in FIG. 14. The intracellular metabolic flux analysis, in simulations, cannot attain metabolic flux that is not existed as a solution statistically. Accordingly, the flux attained above can be considered to be adequate. With the use of the apparatus for evaluation of cellular characteristics in combination with the intracellular metabolic flux analysis, metabolic changes can be perceived more specifically. Thus, information useful for designing a culture vessel (e.g., the consumption rate of each nutrient substrate) can be attained.

<Influence of Shear Stress Level in Batch Culture Vessel on Cellular Metabolism>

Figure 15:
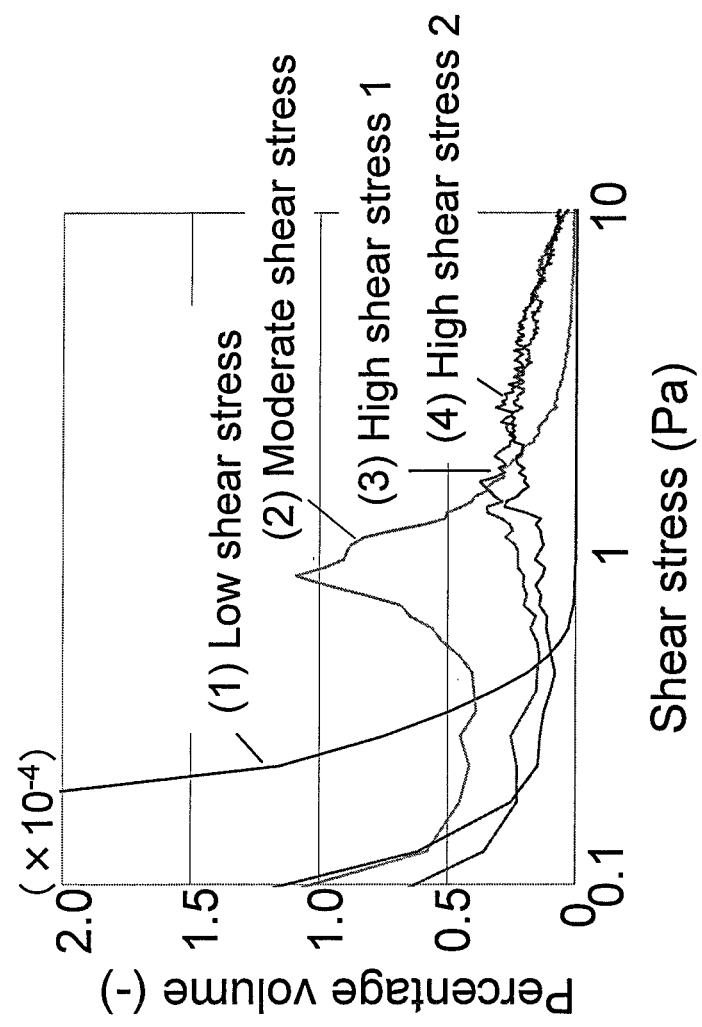
FIG. 15 shows the shear stress distribution in each culture experiment.
Figure 16:
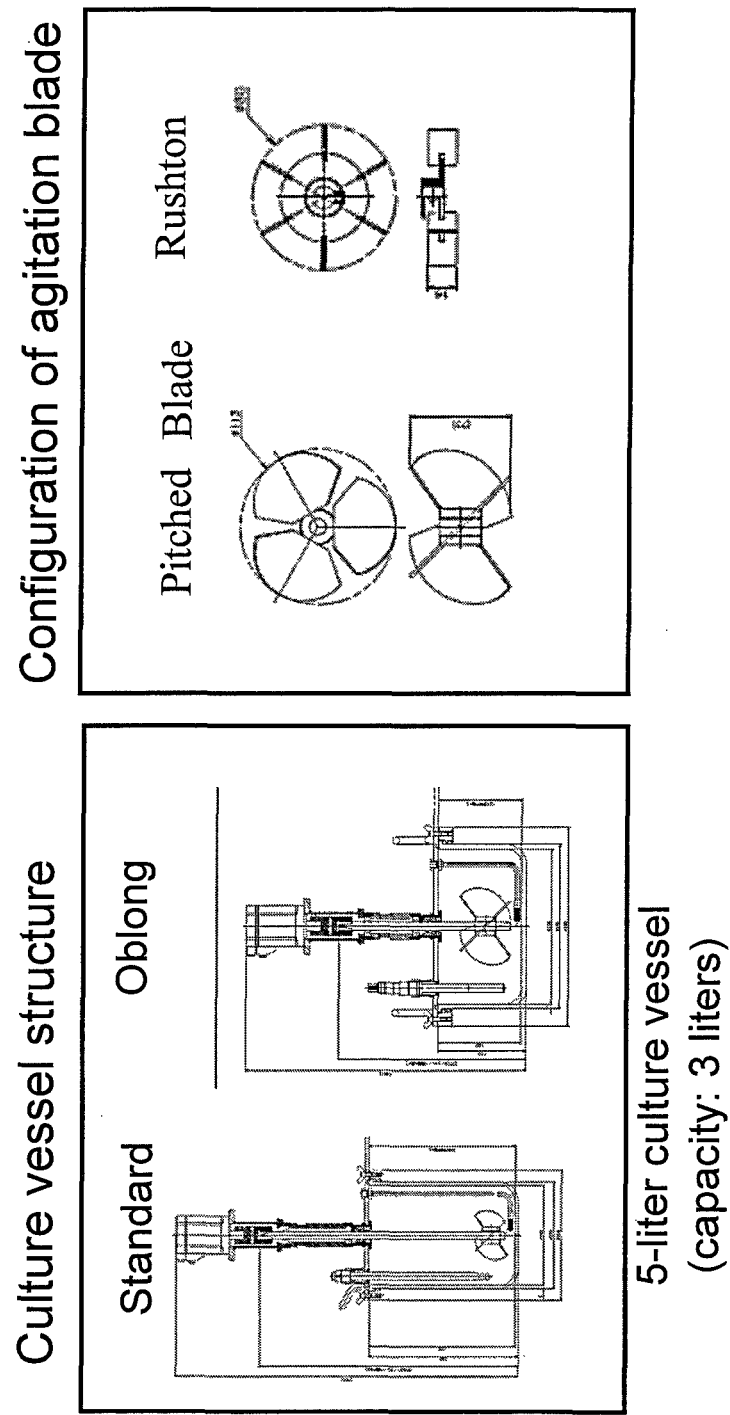
FIG. 16 shows the configuration of the culture tank and that of the agitation blade in each culture experiment.

It was found that changes would occur in cellular metabolism with application of uniform shear stress at around 0.5 Pa to 1 Pa in the micro flow channel (FIG. 12). In the case of cell culture using a culture vessel, however, the shear stress is distributed ununiformaly. In order to inspect whether or not the cellular metabolism changes with the application of high shear stress over 1 Pa in a culture vessel, the "low shear stress conditions" in which shear stress is 0.5 Pa or lower, "moderate shear stress conditions" in which the dominant shear stress is 0.5 Pa to 1 Pa, and two types of shear stress conditions in which the dominant shear stress is over 1 Pa (i.e., "high shear stress conditions 1" and "high shear stress conditions 2") as shown in FIG. 15, were established by adjusting the configurations of culture vessels, the configurations of agitation blades, and the number of revolutions. Culture conditions for each shear stress level are as shown in Table 1, and the configurations of culture vessels and the configurations of agitation blades are as shown in FIG. 16. Specifically, pitched-paddle blades (Pitched Blades) and flat-paddle blades (Rushton) were employed.

TABLE 1

| Conditions | Vessel structure | Blade configuration | Number of evolutions | Percentage volume of 0.5 Pa to 20 Pa |
|---|---|---|---|---|
| Low shear stress conditions | Standard | Pitched blades | 30 rpm | 0% |
| Moderate shear stress conditions | | | 150 rpm | 77% |

TABLE 1-continued

| Conditions | Vessel structure | Blade configuration | Number of evolutions | Percentage volume of 0.5 Pa to 20 Pa |
|---|---|---|---|---|
| High shear stress conditions 1 | Oblong | | 100 rpm | 90% |
| High shear stress conditions 2 | | Rushton | 100 rpm | 90% |

The shear stress distribution was calculated via fluid simulations. In the present experiment, dissolved oxygen was regulated by selectively conducting aeration on a liquid surface without conducting aeration in the solution in order to selectively evaluate the influence of shear stress.

1. Procedures for Culture Experiment 1-1. Cells and Medium

A culture experiment was carried out using Chinese hamster ovary (CHO) cells (CRL-9606 cells for adhesion culture and float culture) producing glycoproteins, and tissue plasminogen activators (tPAs), purchased from the American Type Culture Collection (ATCC). The medium used was prepared by adding fetal bovine serum (FBS) (final concentration: 10%) and antibiotics (penicillin and streptomycin) to the Ham's F12 basal medium.

1-2. Culture Procedures

Culture was conducted using a 1-liter or 3-liter culture vessel under the conditions described in the section above. Cells were seeded at a density of $1 \times 10^5$ cells/ml, and the conditions were regulated to maintain dissolved oxygen concentration at 2.7 mg/l, the pH level at 7.2, and temperature at 37° C. during culture. Aseptic sampling was performed once or twice every day, and components of the culture solution were analyzed.

1-3. Analysis of Components of Culture Solution

The sampled culture solution was analyzed in terms of (1) viable counts, (2) medium components (glucose, glutamine, lactic acid, and ammonia), and (3) the amounts of tPA proteins. The method of analysis is described below.

(1) Viable Cell Counting

Viable cell counting was carried out using the Vi-CELL cell viability analyzer (Beckman Coulter). The cell culture solution was mounted on Vi-CELL, viable cells were distinguished from dead cells via trypan blue staining, and image data was obtained from the cells, followed by automatic counting. Thus, the viable cell count was determined (2) Medium Component Analysis (Glucose, Glutamine, Lactic Acid, and Ammonia)

Glucose, glutamine, lactic acid, and ammonia in the culture solution were assayed using Bioplofile 100 plus (Nova).

(3) Quantification of tPA Proteins

Quantification of tPA proteins was carried out using the tPA, Human, ELISA Kit (Funakoshi). The method of analysis was based on enzyme-linked immunoadsorbent assays (ELISA) with the use of anti-mouse tPA as a primary antibody and biotinylated polyclonal anti-tPA as a secondary antibody. With the use of tetramethylbenzidine as a substrate, the chromogenic reaction was allowed to proceed with the use of streptoavidin and peroxidase, and the absorbance at 450 nm was assayed using an absorptiometer.

Figure 17:
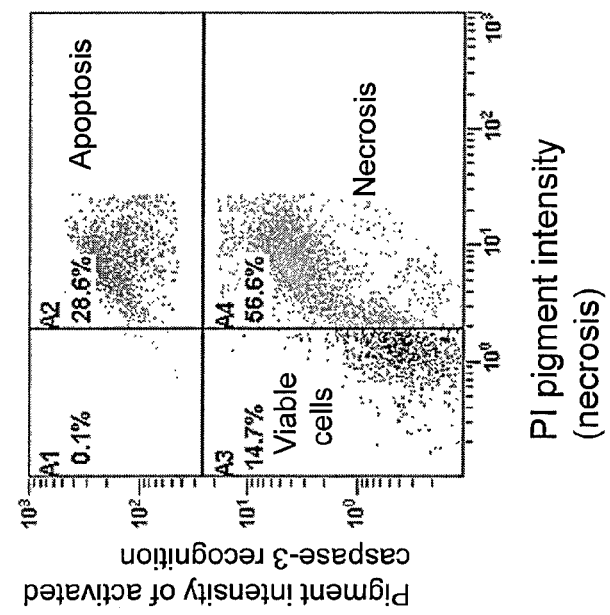
FIG. 17 shows apoptosis detection using a flow cytometer.

(4) Measurement of Percentages of Viable Cells, Apoptotic Cells, and Necrotic Cells The percentages of viable cells, apoptotic cells, and necrotic cells were assayed using a flow cytometer (Beckman Coulter). The culture solution sampled from the culture vessel was mounted on a centrifuge (room temperature, 500×g, 5 minutes) to precipitate the cells. After the cells were washed with a wash solution, the fluorescence-labeled anti-Caspase antibodies were allowed to react therewith at 37° C. for 30 minutes. In order to eliminate excess fluorescence, the cells were washed with a wash solution, an assay buffer was added, a fluorescent dye (propidium iodide (PI)) for necrosis detection was added thereto, and the resultant was analyzed using a flow cytometer. FIG. 17 shows examples of the results of analysis. The cells stained with fluorescent dyes (PI) and anti-Caspase antibodies were determined to be apoptotic cells (region A2 in FIG. 17), the cells not stained with the fluorescent dye (PI) but stained with anti-Caspase antibodies were determined to be necrotic cells (region A4 in FIG. 17), the cells not stained with the fluorescent dye (PI) or anti-Caspase antibodies were determined to be viable cells (region A3 in FIG. 17), and the percentages of these cells were determined.

2. Results of Experiment

Figure 18:
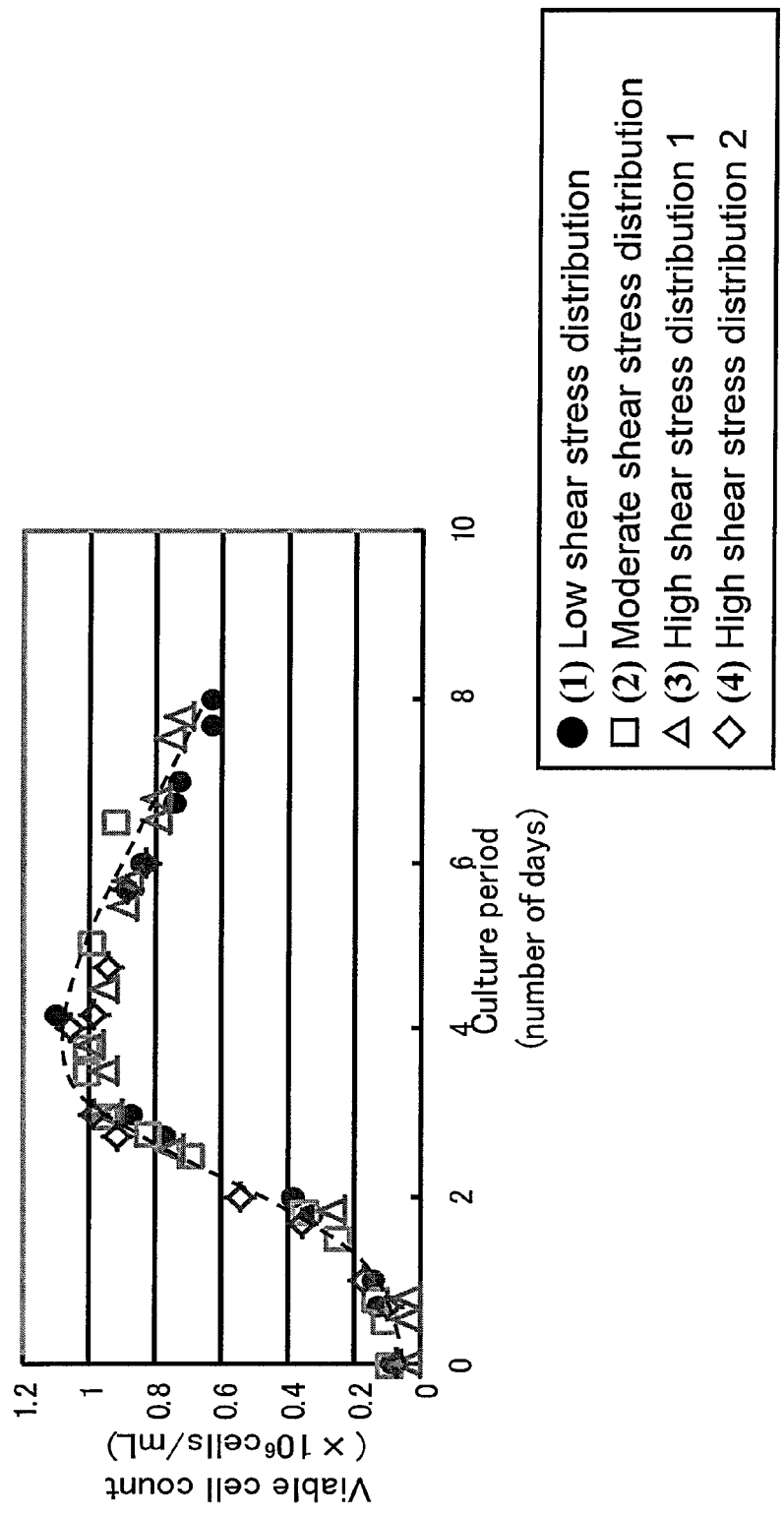
FIG. 18 shows a growth curve attained when cells are cultured at various shear stress levels.

FIG. 18 shows growth curves attained when cells were cultured at various shear stress levels shown in FIG. 15. At the logarithmic growth phase, the growth rate was 0.038 h$^{-1}$ and the peak cell density was $1 \times 10^6$ cells/ml. Such results are consistent with the results of culture conducted with the use of CRL-9606 cells that have been generally reported. No significant differences were observed between any of the various shear stress conditions and the low shear stress conditions simulating general culture conditions.

Figure 19:
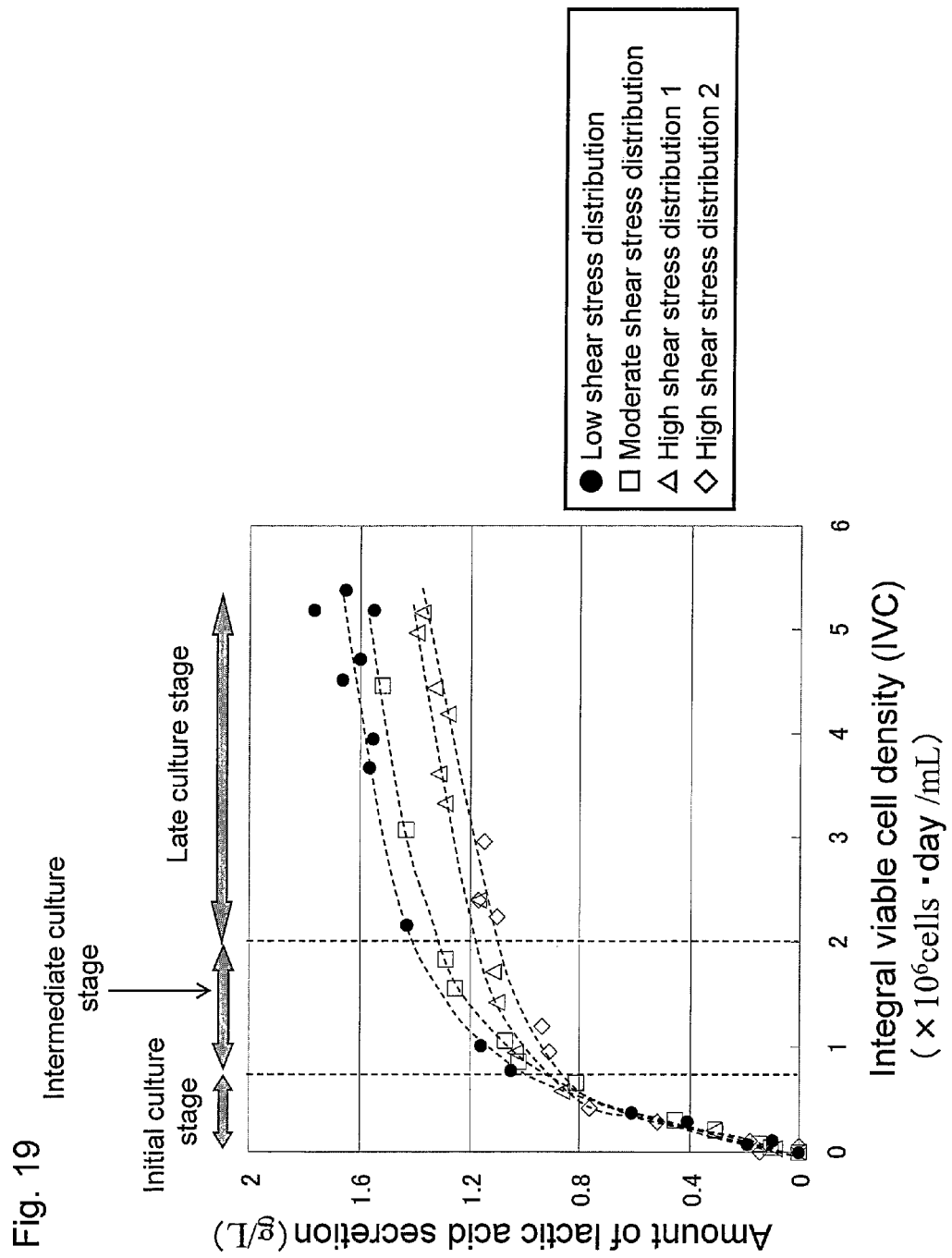
FIG. 19 shows the correlation between the amount of lactic acid secretion and the integral viable cell density.
Figure 20:
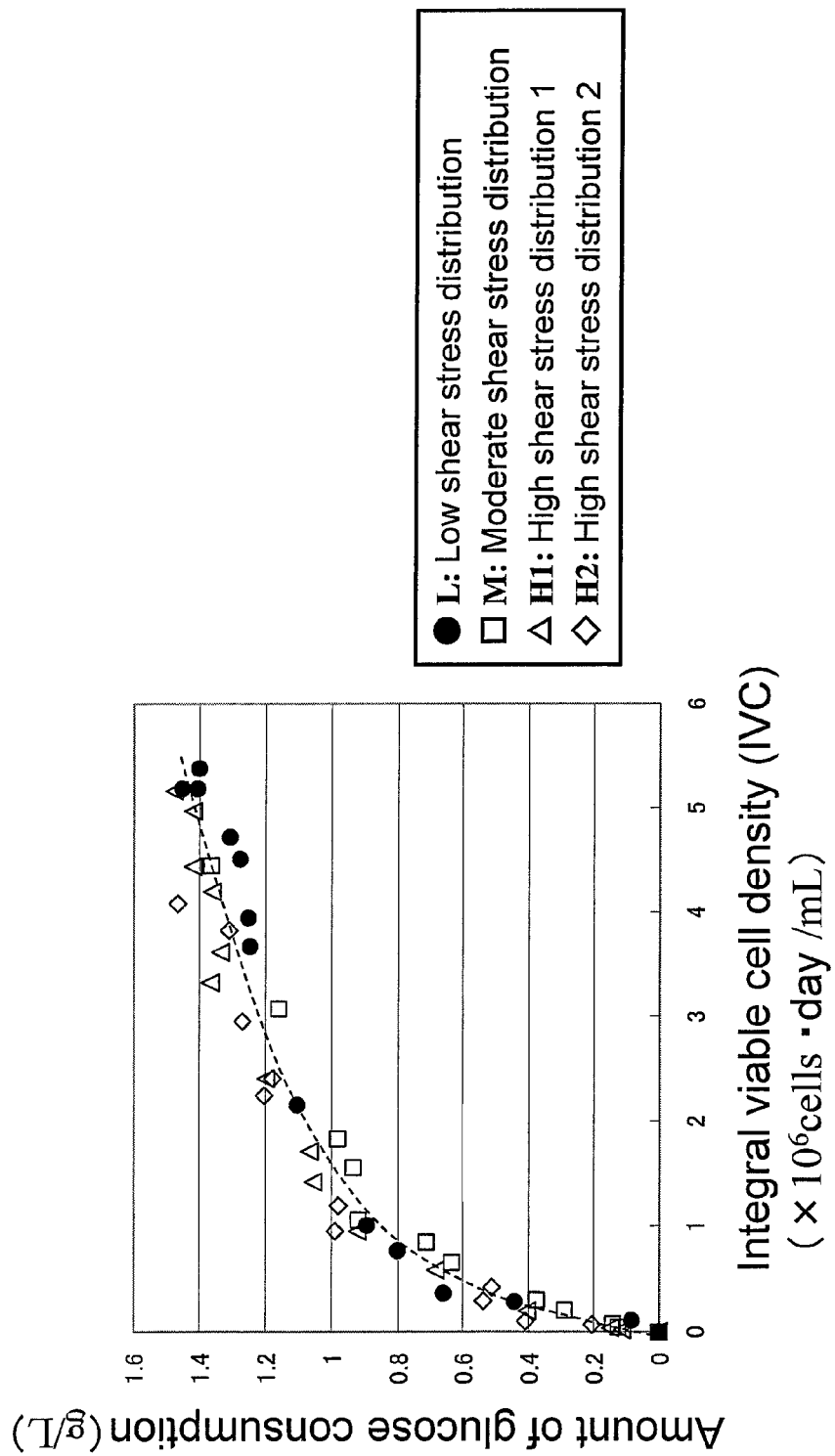
FIG. 20 shows the correlation between the glucose consumption rate and the integral viable cell density.

Concerning cellular metabolism, the correlations between the amount of lactic acid secretion (FIG. 19), the amount of glucose consumption (FIG. 20), the amount of glutamine consumption (FIG. 21), and the amount of ammonia secretion (FIG. 22) and the integral viable cell density corresponding thereto were inspected. Since the horizontal axis of each chart represents the integral viable cell density (IVC), the slope of the chart indicates the substrate consumption rate per unit cell or the metabolite secretion rate per unit cell. According to the correlation between the amount of lactic acid secretion and the integral viable cell density (FIG. 19), the amount of lactic acid secretion decreases as shear stress increases from low shear stress conditions to high shear stress conditions 2. While no significant differences were observed in terms of the lactic acid secretion rate (indicated by the slope of the chart) among various shear stress conditions at the initial culture stage (IVC<$0.6 \times 10^6$ cells·day/ml), significant differences were observed in the lactic acid secretion rate at the intermediate culture stage ($0.6 \times 10^6$ cells·day/ml<IVC<$2 \times 10^6$ cells·day/ml). Thereafter, no differences were observed in the lactic acid secretion rate at the late culture stage ($2 \times 10^6$ cells·day/ml<IVC). The influence of the shear stress distribution on lactic acid secretion depends on the culture phase, although the detailed mechanisms thereof remain unknown.

Figure 21:
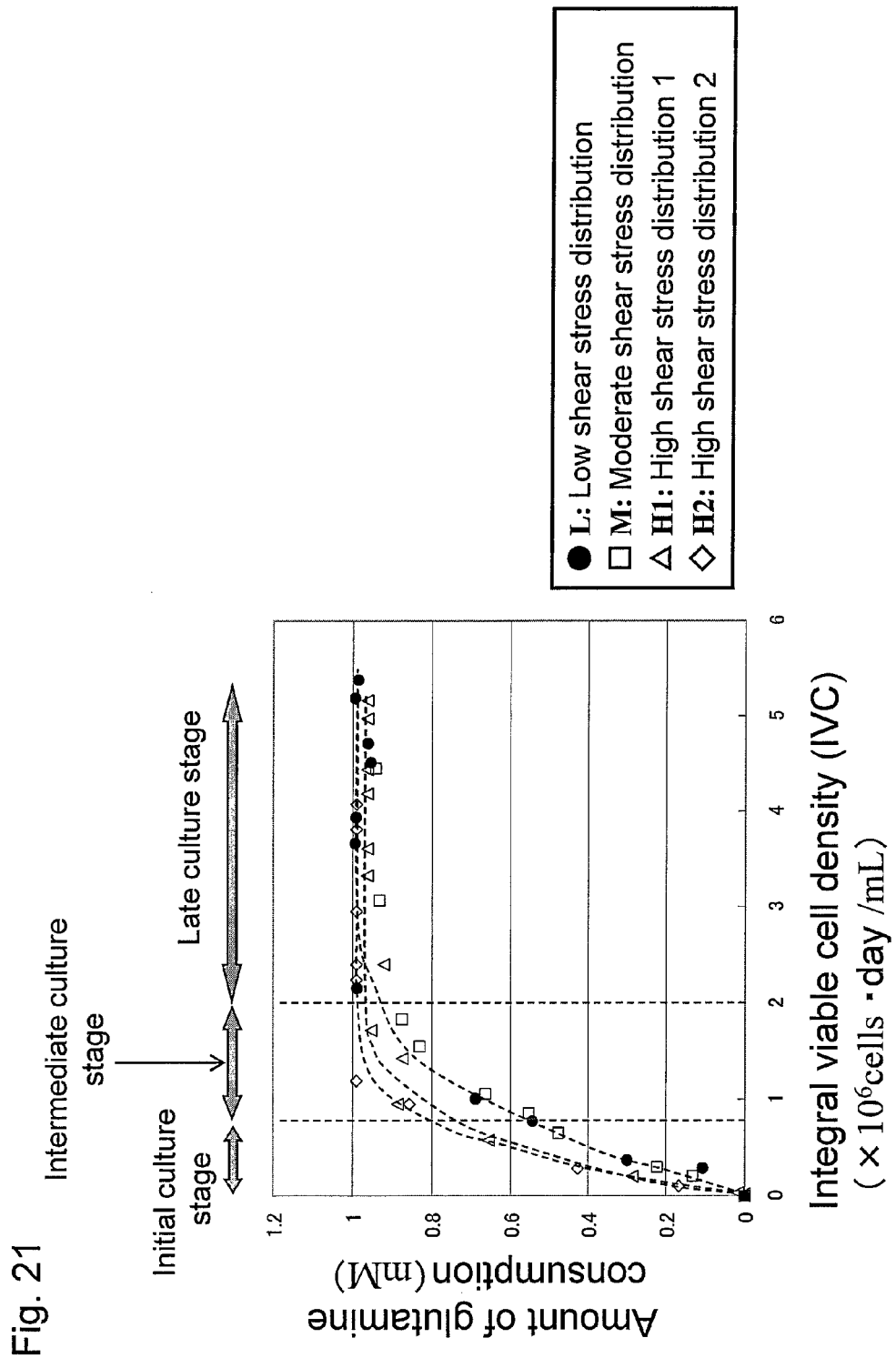
FIG. 21 shows the correlation between the glutamine consumption rate and the integral viable cell density.
Figure 22:
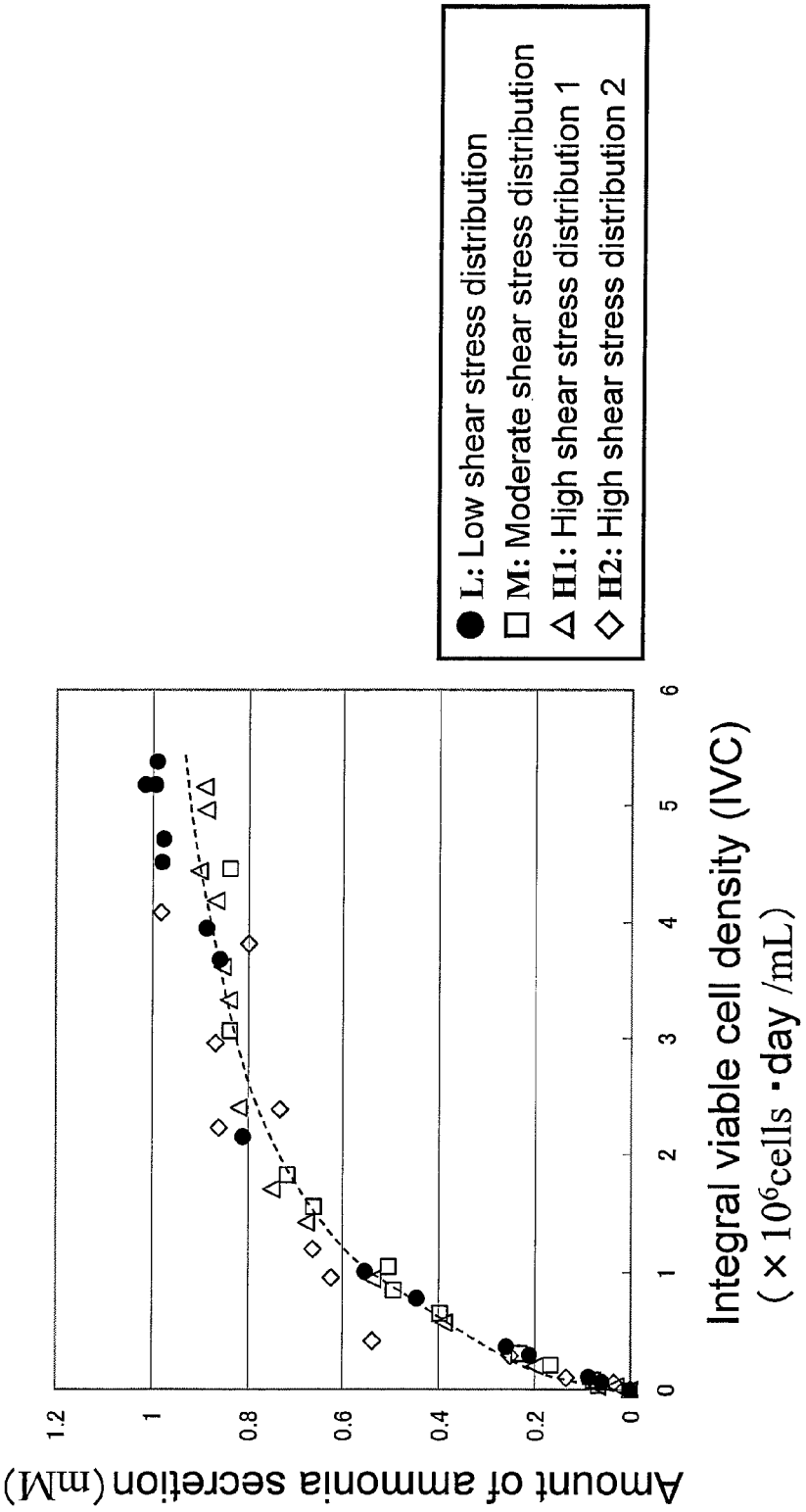
FIG. 22 shows the correlation between the amount of ammonia secretion and the integral viable cell density.

Concerning the consumption rate of glucose serving as a main substrate for lactic acid secretion (FIG. 20), however, no significant differences were observed among various shear stress conditions. That is, the shear stress distribution did not affect the glucose consumption rate. Concerning the correlation between the amount of glutamine consumption and the integral of viable cell counts (FIG. 21), no differences were observed under low shear stress conditions or moderate shear stress conditions (FIG. 21). Under high shear stress conditions 1 and high shear stress conditions 2, the amount of glutamine consumption increased as shear stress increased. The glutamine consumption rate (indicated by the slope of the chart) was increased at the initial culture stage (IVC<$0.6 \times 10^6$ cells·day/ml) and at the intermediate culture stage ($0.6 \times 10^6$ cells·day/ml<IVC<$2 \times 10^6$ cells·day/ml) as the shear stress increased. Since glutamine depletion occurred at the late culture stage ($2\times10^6$ cells/ml·day<IVC), the consumption rate could not be examined. A metabolite generated by glutamine as a main substrate was ammonia. Concerning the correlation between the amount of ammonia secretion and the integral viable cell density (FIG. 22), no significant differences were observed among various shear stress conditions in terms of amount of ammonia secretion and rate of ammonia secretion (indicated by the slope of the chart).

Thus, the lactic acid consumption rate at the intermediate culture stage and the glutamine consumption rate at the initial and intermediate culture stages were found to depend on the shear stress distribution conditions. That is, the lactic acid secretion rate decreased and the glutamine consumption rate increased as shear stress increased. In contrast, the glucose consumption rate and the ammonia secretion rate were not affected by the shear stress distribution conditions. Such results demonstrate that the lactic acid secretion/ glucose consumption rate and the ammonia secretion/glutamine consumption rate decrease as shear stress increases. Accordingly, such results are consistent in terms of qualitative properties with the results of an evaluation performed with the application of uniform shear stress (FIG. 13). The results demonstrate that the production of high-quality, useful substances can be realized while suppressing accumulation of lactic acid that may adversely affect the cell growth and the quality of useful substances to be produced by a culture technique in which a large amount of glutamine is supplied under high shear stress conditions 1 and high shear stress conditions 2. When the shear stress distribution is 0.5 Pa to 20 Pa in 80% or more, and preferably 90% or more of the culture, in particular, the effects thereof are remarkable. A certain level of effects can be attained if shear stress is in such a range in 77% of the culture. Concerning cell growth, depletion of a nutrient substrate had occurred before the effects of lactic acid suppression were exerted according to the batch culture, and remarkable effects were thus not obtained. By improving medium components, however, cell growth could also be improved.

<Influence of the Shear Stress Distribution in Fed-Batch Culture Vessel on Cellular Metabolism>

Fed-batch culture was carried out at the same shear stress level as that used with batch culture. A medium was prepared by analyzing the intracellular metabolic rate in advance and determining the amino acid composition of the medium based on the results of analysis. In the present example, culture conditions at various shear stress levels are as shown in Table 2.

TABLE 2

| Shear stress conditions | Vessel structure (aspect ratio σ/h) | Blade configuration | Number of revolutions |
| --- | --- | --- | --- |
| (1) High shear stress (3 liters) | 2:1 | Rushton | 100 rpm |
| (2) High shear stress (100 liters) | 1:1 | Flat paddle | 70 rpm |
| (3) Low shear stress (1 liter) | 1:1 | Flat paddle | 50 rpm |
| (4) Low shear stress (3 liters) | 2:3 | Pitched blade | 30 rpm |
| (5) Low shear stress (100 liters) | 3:2 | Flat paddle | 20 rpm |

Figure 23:
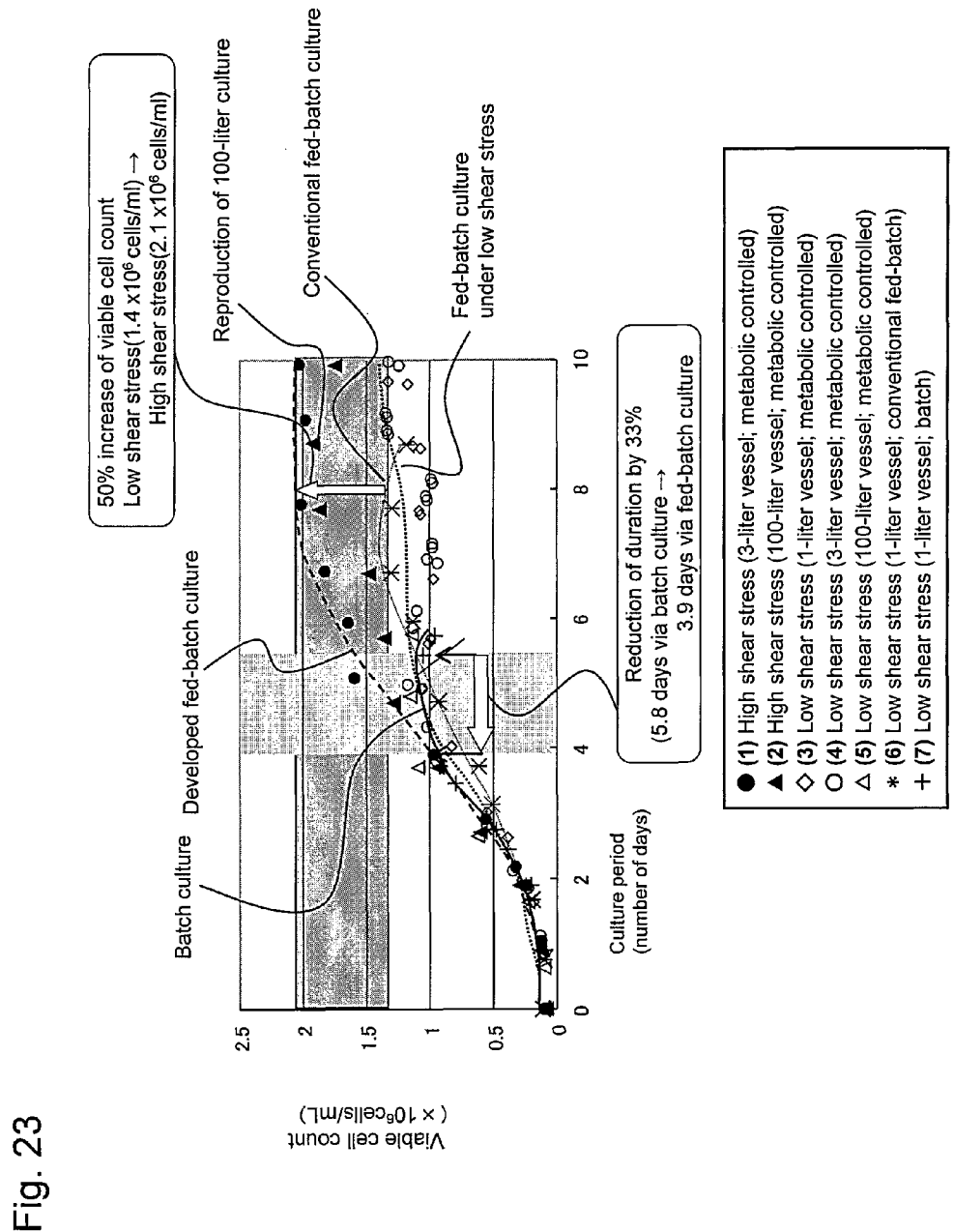
FIG. 23 shows a growth curve for each culture.
Figure 24:
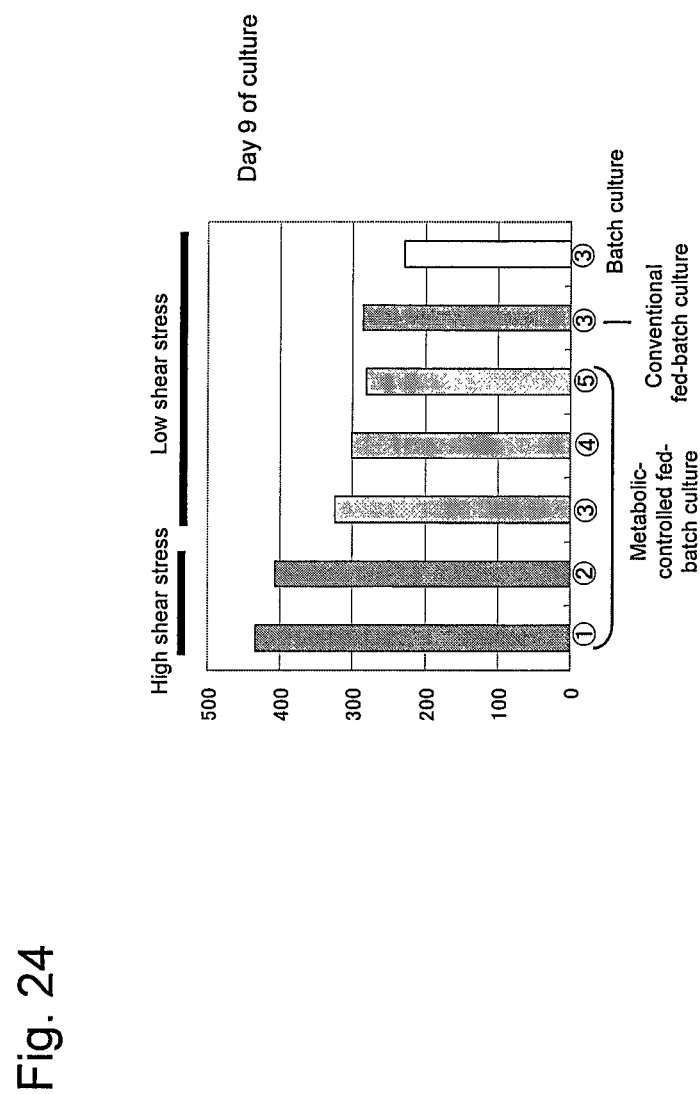
FIG. 24 shows the amount of proteins produced via each culture.
Figure 25:
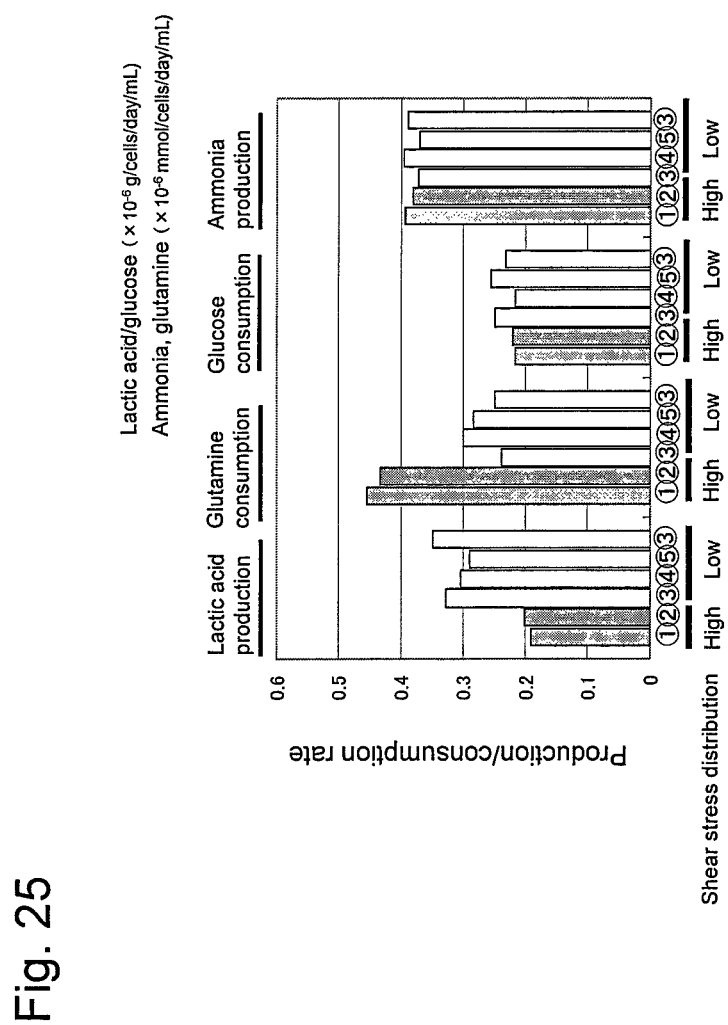
FIG. 25 shows the metabolic rate of each culture.

FIG. 23 shows the growth curve attained via fed-batch culture performed in the present example. The peak cell count was increased by applying high shear stress. With the application of high shear stress, also, the amount of protein production became 1.5 times higher than that attained with the application of low shear stress (compare first chart from the left with the sixth chart from the left in FIG. 24). The metabolic rates in cultures are as shown in FIG. 25, and secretion of a growth inhibitor (i.e., lactic acid) was inhibited at high shear stress. Accordingly, shear stress distribution may be as high as 0.5 Pa to 20 Pa in 80% or more, and preferably 90% or more of the culture, so that intracellular metabolism may be improved, and productivity and product quality may be enhanced.

<Adequate Shear Stress Level for Scale-Up Culture>

With the use of fluid analysis software (R-Flow, R-flow Corporation, Ltd.), the shear stress distribution in a culture vessel can be determined. With the use of fluid analysis software, in particular, the concentration of the culture solution, the viscosity of the culture solution, the configuration of the culture vessel, the configuration of the agitation blade, the wall surface conditions of the culture vessel, and the number of revolutions of the agitation blade may be adequately inputted as variables, so that the shear stress distribution in the culture vessel can be determined. Specifically, the mesh data of the culture vessel may be prepared based on the above conditions (e.g., the aspect ratio of the culture vessel, the configuration of the agitation blade, and the number of revolutions for agitation), and the shear stress distribution in the culture vessel can be calculated using fluid analysis software. When providing meshes, it is preferable that the wall surface conditions of the culture vessel, such as the dissolved oxygen electrode or the baffle, be taken into consideration, so as to improve the uniform shear stress conditions.

Figure 26:
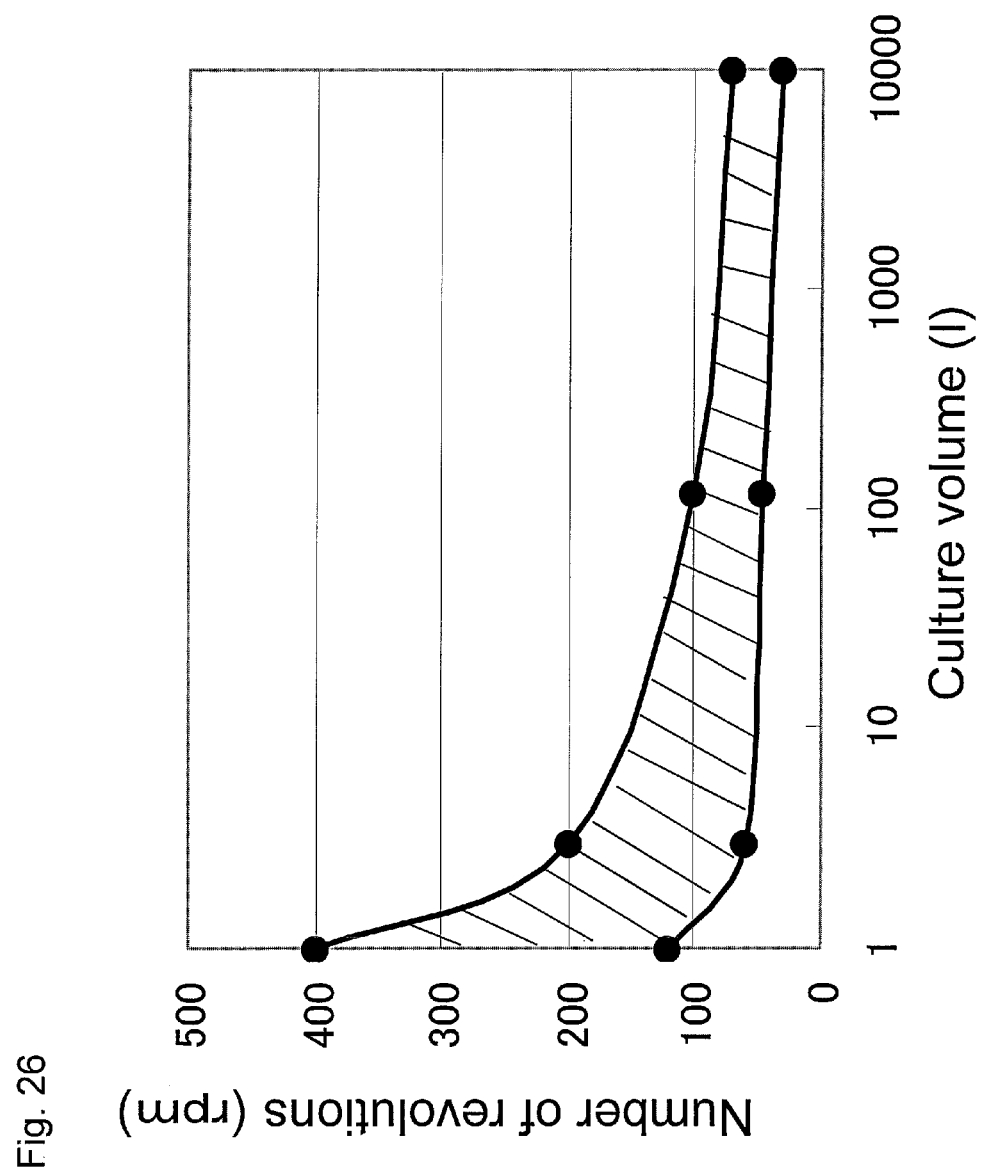
FIG. 26 shows the range of the culture vessel volume and the number of revolutions for agitation that realize the adequate shear stress levels for agitation blades having typical configurations.

The shear stress distribution in a small-scale culture vessel differs from that in a large-scale culture vessel. FIG. 26 shows a range of culture vessel volumes and the number of revolutions for agitation that realizes the adequate shear stress level with the use of agitation blades of typical configurations. In FIG. 26, a region indicated with slanted lines represents a range of culture vessel volume and the number of revolutions for agitation that realizes the condition in which the shear stress distribution is 0.5 Pa to 20 Pa in 90% or more of the culture vessel by volume. As described above, the use of fluid analysis software enables prediction of the number of revolutions that is necessary to realize the condition in which the shear stress distribution is 0.5 Pa to 20 Pa in 90% or more of the increased volume of the culture vessel.

DESCRIPTION OF NUMERICAL REFERENCES

1: culture vessel; 2: agitation blade; 3: medium-containing tank; 4: aseptic sampling unit; 5: assay device; 6: analyzer; 7: control unit; 8: steam generator; 10: flow chamber; 11: dissolved oxygen (DO) measurement unit; 12: medium balancing tank; 14: pulsation damper; 15: PharMed tube; 16: analyzer; 17: liquid delivery pump (Perista Pump); 18: upper member; 19: lower member; 20: space; 21: inlet port; 22: outlet port; 24: DO electrode; 25: space; 26: agitator; 27: medium outflow tube; 28: medium inflow tube; 29: DO electrode

The invention claimed is:

1. A cell culture apparatus comprising:
    a culture vessel comprising of an agitation blade and a drive unit that allows the agitation blade to revolve, wherein the culture vessel has a volume of $1-10^4$ Liters; and
    a control unit that is configured to control the drive unit to realize agitation culture conditions in which the shear stress distribution is 1.0 Pa to 20 Pa in 90% or more of the culture vessel by volume, wherein the control unit is configured to control the drive unit to adjust the number of revolutions for agitation to be within a range of from 50 to 400 rpm.

2. The cell culture apparatus according to claim 1, wherein the shear stress distribution in the culture vessel is determined via fluid analysis.

3. The cell culture apparatus according to claim 2, wherein the fluid analysis comprises calculating the shear stress distribution and the percentage volume using the concentration of the culture solution, the viscosity of the culture solution, the configuration of the culture vessel, the configuration of the agitation blade, the wall surface conditions of the culture vessel, and the number of revolutions of the agitation blade as variables.

4. The cell culture apparatus according to claim 1, wherein the agitation blade comprises a pitched-paddle-shaped agitation blade.

5. The cell culture apparatus according to claim 1, wherein the agitation blade comprises a flat-paddle-shaped agitation blade.

6. A culture control method comprising performing cell culture under agitation culture conditions established by the cell culture apparatus of claim 1 in which the shear stress distribution is 1.0 Pa to 20 Pa in 90% or more of the culture vessel by volume.

7. The culture control method according to claim 6, wherein the shear stress distribution in the culture vessel is determined via fluid analysis.

8. The culture control method according to claim 7, wherein the fluid analysis comprises calculating the shear stress distribution and the percentage volume using the concentration of the culture solution, the viscosity of the culture solution, the configuration of the culture vessel, the configuration of the agitation blade, the wall surface conditions of the culture vessel, and the number of revolutions of the agitation blade as variables.

* * * * *